US008764835B2

(12) United States Patent
Ferree

(10) Patent No.: US 8,764,835 B2
(45) Date of Patent: Jul. 1, 2014

(54) INTERVERTEBRAL DISC TREATMENT METHODS AND APPARATUS

(76) Inventor: Bret A. Ferree, Cincinnati, OH (US)

( * ) Notice: Subject to any disclaimer, the term of this patent is extended or adjusted under 35 U.S.C. 154(b) by 0 days.

(21) Appl. No.: 13/018,968

(22) Filed: Feb. 1, 2011

(65) Prior Publication Data

US 2011/0190893 A1    Aug. 4, 2011

Related U.S. Application Data

(63) Continuation-in-part of application No. 11/811,751, filed on Jun. 12, 2007, now Pat. No. 8,075,619, and a continuation-in-part of application No. 12/263,753, filed on Nov. 3, 2008, and a continuation-in-part of application No. PCT/US2009/065954, filed on Nov. 25, 2009.

(60) Provisional application No. 60/813,232, filed on Jun. 13, 2006, provisional application No. 60/847,649, filed on Sep. 26, 2006, provisional application No. 61/118,246, filed on Nov. 26, 2008, provisional application No. 61/300,993, filed on Feb. 3, 2010.

(51) Int. Cl.
*A61F 2/44* (2006.01)

(52) U.S. Cl.
USPC .......... 623/17.16; 606/279; 606/222; 606/144

(58) Field of Classification Search
USPC ............ 623/17.11–17.16; 606/279, 139, 144, 606/145, 148, 222
See application file for complete search history.

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 4,349,921 A | 9/1982 | Kuntz |
| 4,413,359 A | 11/1983 | Akiyama et al. |

(Continued)

FOREIGN PATENT DOCUMENTS

| | | |
|---|---|---|
| EP | 0277678 | 8/1988 |
| EP | 0700671 | 3/1996 |

(Continued)

OTHER PUBLICATIONS

Wilke, H. et al., New In Vivo Measurements of Pressures in the Intervertebral Disc in Daily Life, Spine, 24(8): 755-762, Nov. 8, 1999.
Proceedings 14th Annual meeting North American Spine Society, Oct. 1999.
Proceedings 13th Annual Meeting North American Spine Society, Oct. 1998.
Goel, V.K., et al., "Mechanical Properties of Lumbar Spinal Motion Segments as Affected by Partial Disc Removal," Spine, 11(10): 1008-1012, (1986).

(Continued)

*Primary Examiner* — Eduardo C. Robert
*Assistant Examiner* — Julianna N Harvey
(74) *Attorney, Agent, or Firm* — Pandiscio & Pandiscio

(57) ABSTRACT

Instrumentation and methods facilitate reconstruction of the anulus fibrosus (AF) and the nucleus pulposus (NP). An intra-aperture component is dimensioned for positioning within a defect in the AF, with one or more components being used to maintain the intra-aperture component in position. The intra-aperture component may be porous and flexible while being intentionally non-expandable in cross section following its positioning within the defect. A component used to maintain the intra-aperture component within the defect includes a flexible longitudinal fixation component that passes through the intra-aperture component and a region of the AF apart from the defect. If available, this may be a region of the AF having overlapping layers with intact fibers in different directions. The flexible longitudinal fixation component may be anchored to one of the upper and lower vertebral bodies.

2 Claims, 20 Drawing Sheets

(56) References Cited

U.S. PATENT DOCUMENTS

| | | |
|---|---|---|
| 4,502,161 A | 3/1985 | Wall |
| 4,512,338 A | 4/1985 | Balko et al. |
| 4,532,926 A | 8/1985 | O'Holla |
| 4,585,458 A | 4/1986 | Kurland |
| 4,663,358 A | 5/1987 | Hyon et al. |
| 4,665,906 A | 5/1987 | Jervis |
| 4,741,330 A | 5/1988 | Hayhurst |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,834,757 A | 5/1989 | Brantigan |
| 4,852,568 A | 8/1989 | Kensey |
| 4,863,477 A | 9/1989 | Monson |
| 4,873,976 A | 10/1989 | Schreiber |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,692 A | 1/1993 | Wilk et al. |
| 5,192,326 A | 3/1993 | Bao et al. |
| 5,222,974 A | 6/1993 | Kensey et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,282,827 A | 2/1994 | Kensey et al. |
| 5,304,194 A | 4/1994 | Chee et al. |
| 5,306,311 A | 4/1994 | Stone et al. |
| 5,312,435 A | 5/1994 | Nash et al. |
| 5,318,780 A | 6/1994 | Viegas et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,697 A | 12/1994 | Baumgartner |
| 5,376,693 A | 12/1994 | Viegas et al. |
| 5,383,477 A | 1/1995 | DeMatteis |
| 5,383,905 A | 1/1995 | Golds et al. |
| 5,390,683 A | 2/1995 | Pisharodi |
| 5,397,331 A | 3/1995 | Himpens et al. |
| 5,397,332 A | 3/1995 | Kammerer et al. |
| 5,405,360 A | 4/1995 | Tovey |
| 5,425,772 A | 6/1995 | Brantigan |
| 5,425,773 A | 6/1995 | Boyd et al. |
| 5,437,631 A | 8/1995 | Janzen |
| 5,456,720 A | 10/1995 | Schultz et al. |
| 5,464,407 A | 11/1995 | McGuire |
| 5,500,000 A | 3/1996 | Feagin et al. |
| 5,507,754 A | 4/1996 | Green et al. |
| 5,514,180 A | 5/1996 | Heggeness et al. |
| 5,520,700 A | 5/1996 | Beyar et al. |
| 5,531,759 A | 7/1996 | Kensey et al. |
| 5,534,028 A | 7/1996 | Bao et al. |
| 5,534,030 A | 7/1996 | Navarro et al. |
| 5,540,715 A | 7/1996 | Katsaros et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,556,428 A | 9/1996 | Shah |
| 5,556,429 A | 9/1996 | Felt |
| 5,562,689 A | 10/1996 | Green et al. |
| 5,562,736 A | 10/1996 | Ray et al. |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,587,175 A | 12/1996 | Viegas et al. |
| 5,591,223 A | 1/1997 | Lock et al. |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,645,084 A | 7/1997 | McKay |
| 5,645,597 A | 7/1997 | Krapiva |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,296 A | 10/1997 | Bryan et al. |
| 5,676,698 A | 10/1997 | Janzen et al. |
| 5,676,701 A | 10/1997 | Yuan et al. |
| 5,681,310 A | 10/1997 | Yuan et al. |
| 5,681,351 A | 10/1997 | Jamiolkowski et al. |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,709,854 A | 1/1998 | Griffith-Cima et al. |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,718,862 A | 2/1998 | Thompson |
| 5,725,577 A | 3/1998 | Saxon |
| 5,728,150 A | 3/1998 | McDonald et al. |
| 5,730,744 A | 3/1998 | Justin et al. |
| 5,733,337 A | 3/1998 | Carr, Jr. et al. |
| 5,743,917 A | 4/1998 | Saxon |
| 5,746,755 A | 5/1998 | Wood et al. |
| 5,746,765 A | 5/1998 | Kleshinski et al. |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,844 A | 7/1998 | Yoon et al. |
| 5,785,705 A | 7/1998 | Baker |
| 5,800,549 A | 9/1998 | Bao et al. |
| 5,800,550 A | 9/1998 | Sertich |
| 5,801,033 A | 9/1998 | Hubbell et al. |
| 5,810,851 A | 9/1998 | Yoon |
| 5,823,994 A | 10/1998 | Sharkey et al. |
| 5,824,008 A | 10/1998 | Bolduc et al. |
| 5,824,082 A | 10/1998 | Brown |
| 5,824,093 A | 10/1998 | Ray et al. |
| 5,824,094 A | 10/1998 | Serhan et al. |
| 5,827,298 A | 10/1998 | Hart et al. |
| 5,827,328 A | 10/1998 | Buttermann |
| 5,836,315 A | 11/1998 | Benderev et al. |
| 5,843,084 A | 12/1998 | Hart et al. |
| 5,846,261 A | 12/1998 | Kotula et al. |

(56) References Cited

U.S. PATENT DOCUMENTS

| | | | |
|---|---|---|---|
| 5,860,425 A | 1/1999 | Benderev et al. | |
| 5,860,977 A | 1/1999 | Zucherman et al. | |
| 5,865,845 A | 2/1999 | Thalgott | |
| 5,865,846 A | 2/1999 | Bryan et al. | |
| 5,879,366 A | 3/1999 | Shaw et al. | |
| 5,888,220 A | 3/1999 | Felt et al. | |
| 5,888,226 A | 3/1999 | Rogozinski | |
| 5,893,889 A | 4/1999 | Harrington | |
| 5,916,225 A | 6/1999 | Kugel | |
| 5,919,235 A | 7/1999 | Husson et al. | |
| 5,922,026 A | 7/1999 | Chin | |
| 5,928,284 A | 7/1999 | Mehdizadeh | |
| 5,935,147 A | 8/1999 | Kensey et al. | |
| 5,954,716 A | 9/1999 | Sharkey et al. | |
| 5,954,767 A | 9/1999 | Pajotin et al. | |
| 5,957,939 A | 9/1999 | Heaven et al. | |
| 5,972,000 A | 10/1999 | Beyar et al. | |
| 5,972,007 A | 10/1999 | Sheffield et al. | |
| 5,972,022 A | 10/1999 | Huxel | |
| 5,976,174 A | 11/1999 | Ruiz | |
| 5,976,186 A | 11/1999 | Bao et al. | |
| 5,980,504 A | 11/1999 | Sharkey et al. | |
| 6,001,130 A | 12/1999 | Bryan et al. | |
| 6,007,570 A | 12/1999 | Sharkey et al. | |
| 6,007,575 A | 12/1999 | Samuels | |
| 6,019,793 A | 2/2000 | Perren et al. | |
| 6,024,754 A | 2/2000 | Engelson | |
| 6,027,527 A | 2/2000 | Asano et al. | |
| 6,126,682 A | 10/2000 | Sharkey et al. | |
| 6,140,452 A | 10/2000 | Felt et al. | |
| 6,146,380 A | 11/2000 | Racz et al. | |
| 6,180,848 B1 | 1/2001 | Flament et al. | |
| 6,183,518 B1 | 2/2001 | Ross et al. | |
| 6,206,921 B1 | 3/2001 | Guagliano et al. | |
| 6,224,630 B1 | 5/2001 | Bao et al. | |
| 6,245,107 B1 | 6/2001 | Ferree | |
| 6,371,990 B1 | 4/2002 | Ferree | |
| 6,402,750 B1 | 6/2002 | Atkinson et al. | |
| 6,425,919 B1 | 7/2002 | Lambrecht | |
| 6,428,576 B1 | 8/2002 | Haldimann | |
| 6,436,143 B1 | 8/2002 | Ross et al. | |
| 6,482,235 B1 | 11/2002 | Lambrecht et al. | |
| 6,511,491 B2 | 1/2003 | Grudem et al. | |
| 6,733,531 B1 | 5/2004 | Trieu | |
| 6,878,167 B2 | 4/2005 | Ferree | |
| 6,893,448 B2 * | 5/2005 | O'Quinn et al. | 606/139 |
| 7,004,970 B2 | 2/2006 | Cauthen, III et al. | |
| 7,201,774 B2 | 4/2007 | Ferree | |
| 7,338,525 B2 | 3/2008 | Ferree | |
| 7,749,250 B2 * | 7/2010 | Stone et al. | 606/232 |
| 7,947,080 B2 | 5/2011 | Ferree | |
| 2002/0123750 A1 | 9/2002 | Eisermann et al. | |
| 2002/0189622 A1 * | 12/2002 | Cauthen et al. | 128/898 |
| 2002/0198599 A1 | 12/2002 | Haldimann | |
| 2003/0074075 A1 | 4/2003 | Thomas et al. | |
| 2003/0114930 A1 | 6/2003 | Lim et al. | |
| 2003/0158604 A1 * | 8/2003 | Cauthen et al. | 623/17.16 |
| 2004/0260397 A1 | 12/2004 | Lambrecht et al. | |
| 2005/0125071 A1 | 6/2005 | Nahleili | |
| 2005/0143826 A1 | 6/2005 | Zucherman et al. | |
| 2006/0217747 A1 | 9/2006 | Ferree | |
| 2007/0067040 A1 | 3/2007 | Ferree | |
| 2007/0135920 A1 | 6/2007 | Ferree | |
| 2007/0167951 A1 | 7/2007 | Ainsworth et al. | |
| 2007/0276494 A1 | 11/2007 | Ferree | |
| 2007/0288040 A1 | 12/2007 | Ferree | |
| 2008/0177298 A1 | 7/2008 | Zucherman et al. | |
| 2010/0016889 A1 | 1/2010 | Ferree | |
| 2011/0034975 A1 | 2/2011 | Ferree | |

FOREIGN PATENT DOCUMENTS

| | | |
|---|---|---|
| EP | 0722700 | 12/1998 |
| EP | 1719463 | 11/2006 |
| EP | 1787604 | 5/2007 |
| FR | 2639823 | 6/1990 |
| WO | WO 95/31946 | 11/1995 |
| WO | WO 95/34331 | 12/1995 |
| WO | WO 97/26847 | 7/1997 |
| WO | WO 97/30638 | 8/1997 |
| WO | WO 98/17190 | 4/1998 |
| WO | WO 98/20939 | 5/1998 |
| WO | WO 98/34552 | 8/1998 |
| WO | WO 99/00074 | 1/1999 |
| WO | WO 99/02108 | 1/1999 |
| WO | WO 99/02214 | 1/1999 |
| WO | WO 99/03422 | 1/1999 |
| WO | WO 99/30651 | 6/1999 |
| WO | WO 99/47058 | 9/1999 |
| WO | WO 99/61084 | 12/1999 |
| WO | WO 99/61840 | 12/1999 |
| WO | WO 99/62439 | 12/1999 |
| WO | WO 00/42953 | 7/2000 |
| WO | WO 00/62832 | 10/2000 |
| WO | WO 01/10316 | 2/2001 |
| WO | WO 01/10318 | 2/2001 |
| WO | WO 01/21246 | 3/2001 |
| WO | WO 01/28464 | 4/2001 |
| WO | WO 01/45577 | 6/2001 |
| WO | WO 2010/062971 | 6/2010 |

OTHER PUBLICATIONS

Ahlgren, B.D., et al., "Anular Incision Technique on the Strength and Multidirectional Flexibility of the Healing Intervertebral Disc," Spine, 19(8): 948-954, (1994).

Barr, J.S., "Ruptured Intervertebral Disc and Sciatic Pain," J. of Bone and Joint Surgery, 29, (2): 429-437 (1947).

Postacchini, F., "Spine Update Results of Surgery Compared With Conservative Management for Lumbar Disc Herniations," Spine, 21 (11): 1383-1387, (1996).

Rogers, L.A., "Experience with Limited versus Extensive Disc Removal in Patients Undergoing Microsurgical Operations for Rupertured Lumbar Discs," Neurosurgery, 22 (1): 82-85, (1988).

Brinckmann, P., et al., "Change of Disc Height, Radial Disc Bulge, and Intradiscal Pressure From Discectomy An in Vitro Investigation on Human Lumbar Discs," Spine, 16(6): 641-646, (1991).

Balderston, R.A., et al., "The Treatment of Lumbar Disc Herniation: Simple Fragment Excision Versus Disc Space Curettage," J. of Spinal Disorders, 4(1): 22-25 (1991).

Hanley, E.N., Jr., et al., "The Development of Low-Back Pain after Excision of a Lumbar Disc," J. of Bone and Joint Surgery, 71A(5): 719-721, (1989).

Tulberg, T., et al., "Incision of the Annulus Fibrosus Induces Nerve Root Morphologic, Vascular and Functional Changes," Spine, 18(7): 843-850, (1993).

Heggeness, M.H., et al., "Discography of Lumbar Discs After Surgical Treatment for Disc Herniation," Spine, 22(14): 1606-1609, (1997).

Kayama, S., et al, "Incision of the Anulus Fibrosus Induces Nerve Root Morphologic Vascular and Functional Changes," Spine, 21(22): 2539-2543, (1996).

Tibrewal, S.B., et al., "Lumbar Intervertebral Disc Heights in Normal Subjects and Patients with Disc Herniation," Spine, 10 (5): 452-454, (1985).

Cauthen, Joseph, C., M.D., "Microsurgical Annular Reconstruction (Annuloplasty) Following Lumbar Microdiscectomy; Preliminary Report of a New Technique," Abstract for Poster Presentation, AANS/CNS Section on Disorders of the Spine and Peripheral Nerves Annual Meeting, 1999.

Husson, J. et al., Inter-Somatic Nucleoplasty by Posterior Path During Disectomy, Concept and Experimental Study, 1998.

\* cited by examiner

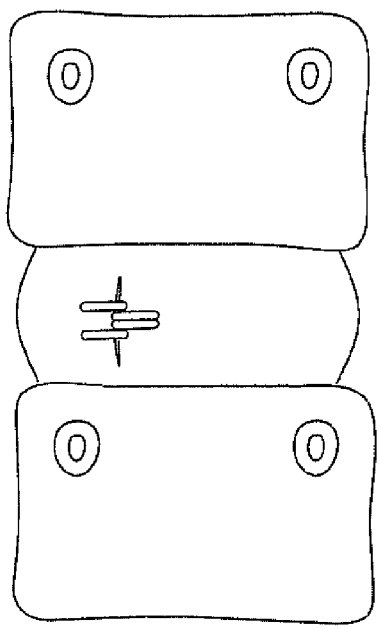
Fig - 4C
Fig - 5B    Fig - 6B
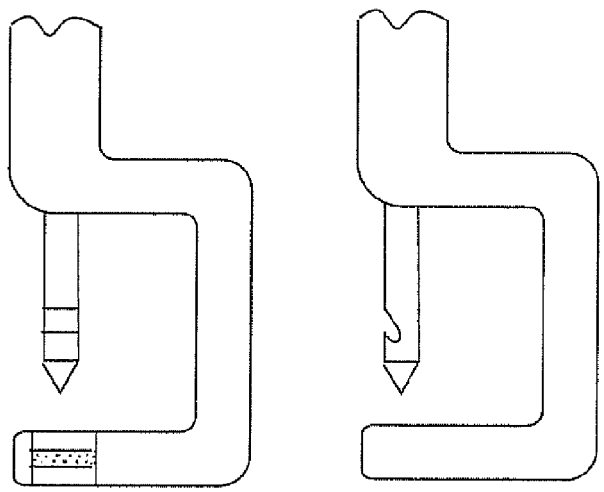
Fig - 6A    Fig - 5A
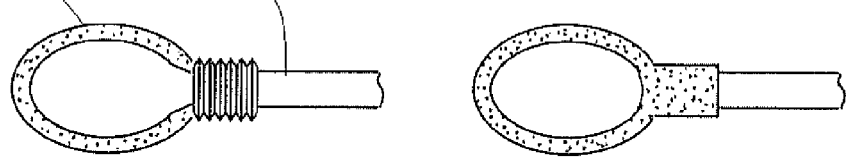
Fig - 7A    Fig - 7B

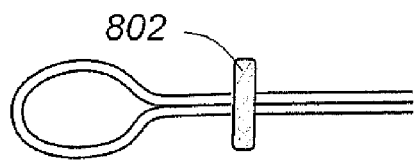
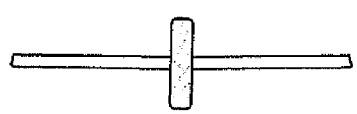
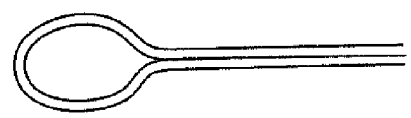
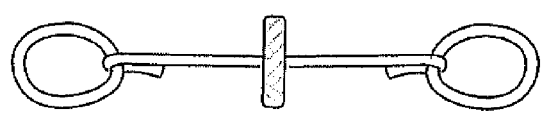
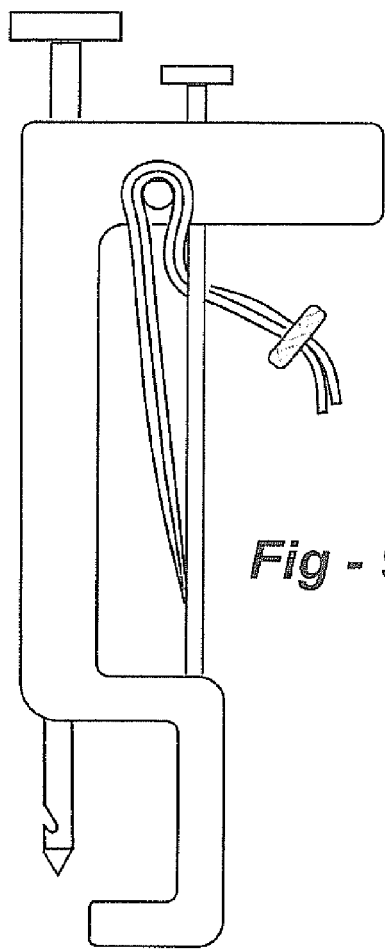
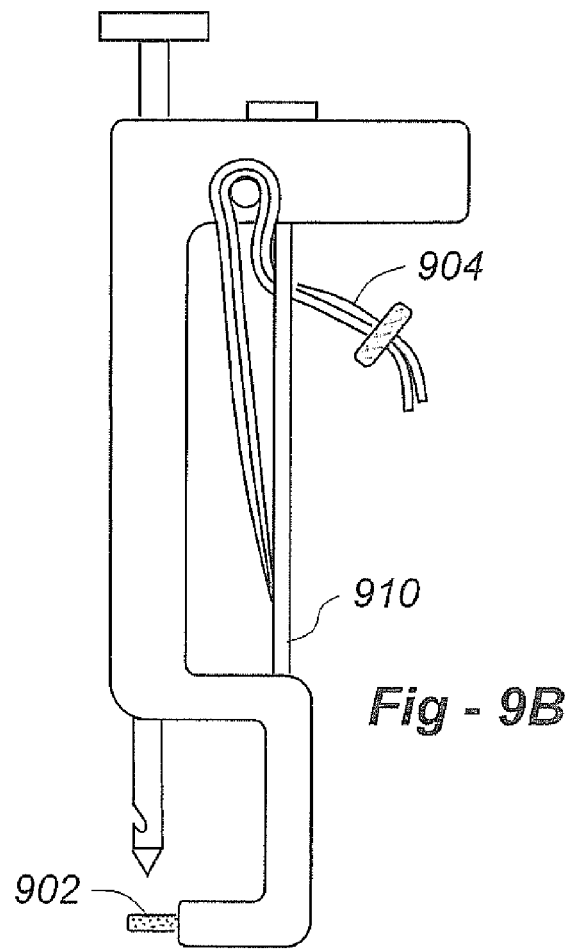

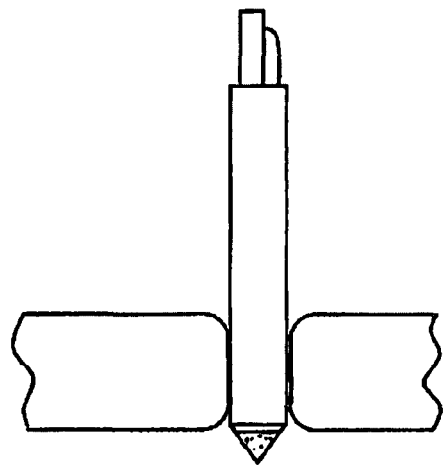
*Fig - 12A*
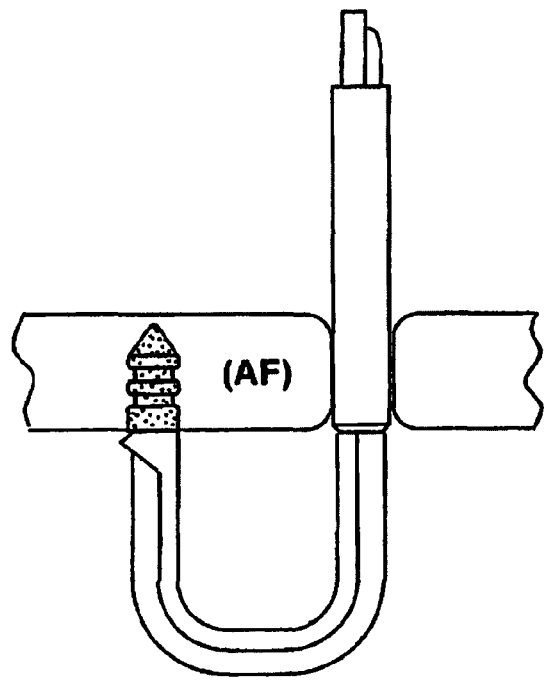
*Fig - 12B*
*Fig - 12C*
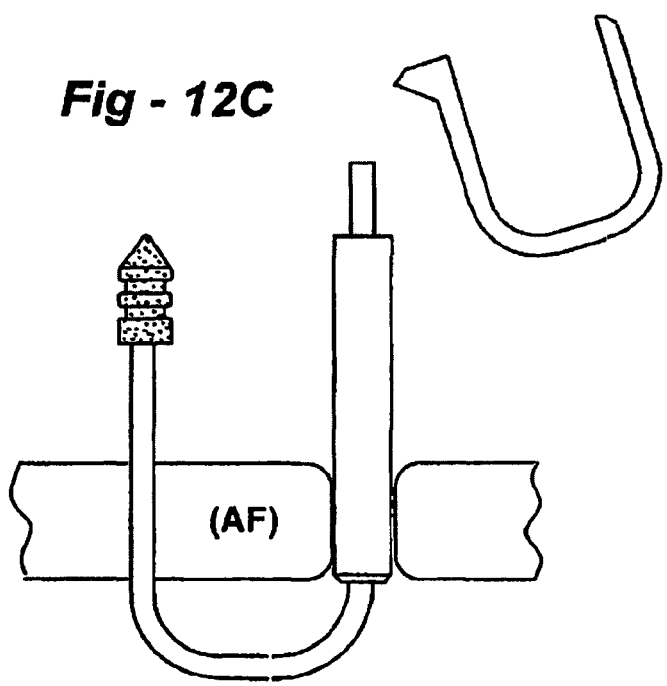
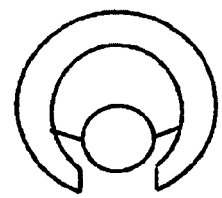
*Fig - 12D*

INTERVERTEBRAL DISC TREATMENT METHODS AND APPARATUS

REFERENCE TO RELATED APPLICATIONS

This U.S. patent application claims priority from U.S. provisional patent application Ser. No. 61/300,993, filed Feb. 3, 2010. This U.S. patent application is also a continuation-in-part of PCT/US2009/065954, filed Nov. 25, 2009, which is a Box VI priority application of U.S. provisional patent application 61/118,246, filed Nov. 26, 2008. This U.S. patent application is also a continuation-in-part of U.S. patent application Ser. No. 12/263,753, filed Nov. 3, 2008, which claims priority from U.S. provisional patent application Ser. No. 60/984,657, filed Nov. 1, 2007. This application is also a continuation-in-part of U.S. patent application Ser. No. 11/811,751, filed Jun. 12, 2007, which claims priority from U.S. provisional patent application Ser. No. 60/813,232, filed Jun. 13, 2006 and U.S. provisional patent application Ser. No. 60/847,649, filed Sep. 26, 2006. The entire content of each application is incorporated herein by reference.

FIELD OF THE INVENTION

This invention relates generally to the treatment of intervertebral disc herniation and degenerative disc disease and, in particular, to apparatus and methods for fortifying and/or replacing disc components such as the anulus fibrosis.

BACKGROUND OF THE INVENTION

The human intervertebral disc is an oval to kidney bean-shaped structure of variable size depending on the location in the spine. The outer portion of the disc is known as the anulus fibrosus (AF, also known as the "anulus fibrosis"). The anulus fibrosus (AF) is made of ten to twenty collagen fiber lamellae. The collagen fibers within a lamella are parallel. Successive lamellae are oriented in alternating directions. About 48 percent of the lamellae are incomplete, but this value varies based upon location and increases with age. On average, the lamellae lie at an angle of sixty degrees with respect to the vertebral axis line, but this too varies depending upon location. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. A high water content (approximately 70-80 percent) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85 percent at birth to approximately 70 percent in the elderly. The ratio of chondroitin sulfate to keratin sulfate decreases with age, while the ratio of chondroitin 6 sulfate to chondroitin 4 sulfate increases with age. The distinction between the anulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and anulus functions are compromised. The nucleus becomes thinner and less able to handle compression loads. The anulus fibers become redundant as the nucleus shrinks. The redundant anular fibers are less effective in controlling vertebral motion. This disc pathology can result in: 1) bulging of the anulus into the spinal cord or nerves; 2) narrowing of the space between the vertebra where the nerves exit; 3) tears of the anulus as abnormal loads are transmitted to the anulus and the anulus is subjected to excessive motion between vertebra; and 4) disc herniation or extrusion of the nucleus through complete anular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either removes the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the anulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in co-pending U.S. Pat. Nos. 6,878,167 and 7,201,774, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often allies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

SUMMARY OF THE INVENTION

The invention broadly facilitates reconstruction of the anulus fibrosus (AF) and the nucleus pulposus (NP). Such reconstruction prevents recurrent herniation following microlumbar discectomy. The invention may also be used in the treatment of herniated discs, anular tears of the disc, or disc degeneration, while enabling surgeons to preserve the contained nucleus pulposus. The methods and apparatus may be used to treat discs throughout the spine including the cervical, thoracic, and lumbar spines of humans and animals.

The invention also enables surgeons to reconstruct the anulus fibrosus and replace or augment the nucleus pulposus. Novel nucleus replacements (NR) may be added to the disc. Anulus reconstruction prevents extrusion of the nucleus replacements through holes in the anulus fibrosus. The nucleus replacements and the anulus fibrosus reconstruction prevent excessive pressure on the anulus fibrosus that may cause back or leg pain. The nucleus replacements may be made of natural or synthetic materials. Synthetic nucleus replacements may be made of, but are not limited to, polymers including polyurethane, silicon, hydrogel, or other elastomers.

Preferred embodiments of the invention include an intra-aperture component dimensioned for positioning within a defect in the AF, with one or more components being used to maintain the intra-aperture component in position. The intra-aperture component may be porous and flexible while being intentionally non-expandable in cross section following its positioning within the defect. A component used to maintain the intra-aperture component within the defect includes a flexible longitudinal fixation component that passes through the intra-aperture component and a region of the AF apart from the defect. If available, this may be a region of the AF having overlapping layers with intact fibers in different directions.

The flexible longitudinal fixation component may be anchored to one of the upper and lower vertebral bodies. The components used to maintain the intra-aperture component within the defect includes a flexible longitudinal fixation component that passes twice through the intra-aperture component and is anchored to one of the upper and lower vertebral bodies. For example, the flexible longitudinal fixation component may form one or more loop or loops, each passing once through the AF and twice through the intra-aperture component.

Portions of the flexible longitudinal fixation components, such as the ends, are passed through the AF with novel instruments. Generally the distal end(s) of the flexible longitudinal fixation components are passed beyond the inner layer of the AF through an aperture in the AF. A portion of the flexible longitudinal fixation component is then pulled, in an inside to outside direction, through one or more holes in the AF tissue adjacent to the aperture. A portion of the flexible longitudinal fixation component generally courses parallel to the inner layer of the AF and through an intra-aperture component. The flexible longitudinal fixation component may be passed through a handle component retained in a releasable fastening feature at the tip of the novel instrumentation.

BRIEF DESCRIPTION OF THE DRAWINGS

FIG. 4C is a posterior view of a coronal cross section of a portion of the spine and the embodiment of the invention drawn in FIG. 3C;
FIG. 5A is a lateral view of the distal end of the an alternative embodiment of the invention drawn in FIG. 1A;
FIG. 5B is a lateral view of the embodiment of the invention drawn in FIG. 5A;
FIG. 6A is lateral view of the distal end of an alternative embodiment of the invention drawn in FIG. 5A;
FIG. 6B is a lateral view of the embodiment of the invention drawn in FIG. 6A;
FIG. 7A is a lateral view of the distal end of an alternative embodiment of the invention drawn in FIG. 3A;
FIG. 7B is a lateral view of an alternative embodiment of the invention drawn in FIG. 7A;
FIG. 8A is a lateral view of an alternative embodiment of the invention drawn in FIG. 3B;
FIG. 8B is lateral view of the embodiment of the invention drawn in FIG. 8A;

FIG. 8C is an exploded lateral view of the embodiment of the invention drawn in FIG. 8B;

FIG. 8D is a lateral view of the embodiment of the invention drawn in FIG. 8B;

FIG. 9A is a lateral view of an alternative embodiment of the invention drawn in FIG. 1A;

FIG. 9B is a lateral view of the embodiment of the invention drawn in FIG. 9A;

FIG. 12A is a lateral view of the distal end of an alternative embodiment of the invention drawn in FIG. 11A and a cross section of the AF;

FIG. 12B is a lateral view of the distal end of the embodiment of the invention drawn in FIG. 12A and a cross section of the AF;

FIG. 12C is an exploded lateral view of the embodiment of the invention drawn in FIG. 12B and a cross section of the AF;

FIG. 12D is superior view of a transverse cross section of the embodiment of the invention drawn in FIG. 12B;

DETAILED DESCRIPTION OF THE INVENTION

Figure 1A:
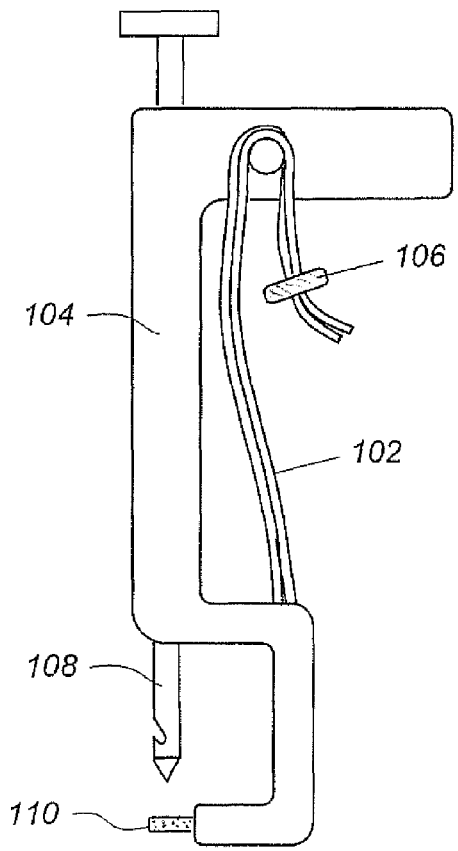
FIG. 1A is a lateral view of the preferred embodiment of the invention.

FIG. 1A is a lateral view of the preferred embodiment of the invention that may be used to pass the ends of the flexible longitudinal fixation component or the central portion of such flexible component through the AF. The Figure represents an alternative embodiment of FIG. 3A of my co-pending application PCT/US2009/065954, the entire content of which is incorporated herein by reference. The flexible longitudinal fixation component 102 is passed through a handle component 104. The handle component is pressed into a releasable fastening feature at the tip of the footplate at the distal end of the tool. The first and second arms of the flexible longitudinal fixation component also pass through a slot like opening on the bottom and posterior portions to the footplate of the instrument and wraps around a projection on the handle of the instrument. The first and second arms of the flexible longitudinal fixation component are then pressed into a releasable fastening feature on the handle of the instrument.

The intra-aperture component 106 and the aims of the flexible longitudinal fixation component are seen hanging from the handle of the instrument. A needle-like component 108 passes through a cannulated shaft through the instrument. The tip of the needle preferably has a tapered point rather than a cutting point. A hook-like opening is seen on the side of the needle component near the distal end of the component.

The footplate is preferably 2 to 8 millimeters long, 1 to 8 millimeters wide, and 1 to 8 millimeters tall. The vertical member attached to the footplate is preferably 3 to 25 millimeters long. The instrument is preferably 20 to 40 centimeters long. The needle-like component is preferably 1 to 2 millimeters in diameter. Alternatively, the needle-like component may be 0.5, 0.6, 0.7, 0.8, 0.9, 2.1, 2.2, 2.3, 2.4, or less than 0.5 or more than 2.4 millimeters in alternative embodiments of the invention. The instrument is preferably made of metal such as steel or titanium. The handle component preferably extends 0.5 to 6 millimeters beyond the tip of the footplate.

Figure 1B:
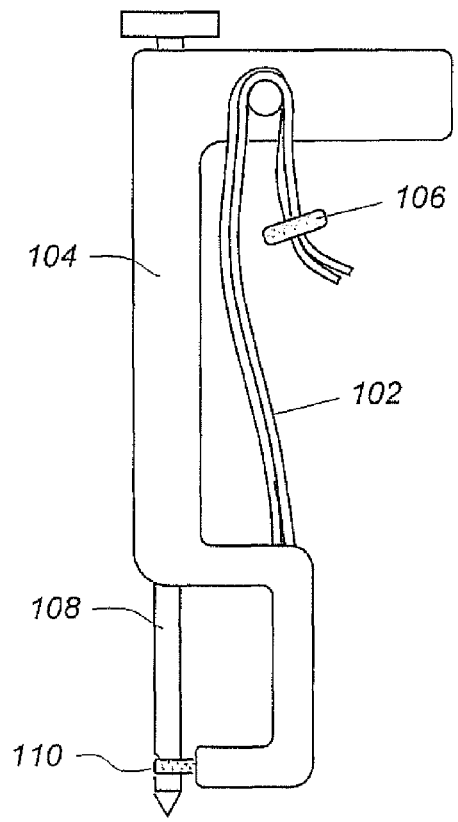
FIG. 1B is a second lateral view of the preferred embodiment of the invention.

FIG. 1B is a second lateral view of the embodiment of the invention drawn in FIG. 1A. The needle component was advanced through the shaft of the tool. The needle component preferably has a feature that prevents axial rotation of the needle relative to the shaft of the tool. For example, the shaft of the tool may have a projection that cooperates with a slot in the side of the cannulated portion of the tool to prevent such axial rotation. The feature keeps the hook-like opening in the side of the needle facing the distal end of the handle component within the footplate portion of the instrument. The center of the opening in the handle component is preferably closer to the footplate than the tip of the needle component. However, the tip of the needle component still passes through the opening in the handle component.

The needle component is preferably actuated by a compressible pistol grip mechanism in an alternative embodiment of the invention. Squeezing the pistol grip advances the needle component in the cannulated component in the alternative embodiment of the invention. The distal portion of the needle forces the handle component to the side and deforms the flexible, elastic component as the needle passes through the handle component. For example, the circular opening through the handle component may become elongated or oval shaped as the needle is passed through the opening in the handle component. Tension on the deformed handle component causes the handle component to migrate into the hook-like opening in the needle-like component of the tool. For example, the deformed, oval shaped handle component may return to its resting, circular shape. The distal portions of the arms flexible longitudinal component are held by the slot in the handle of the instrument as the handle component is deformed.

Figure 1C:
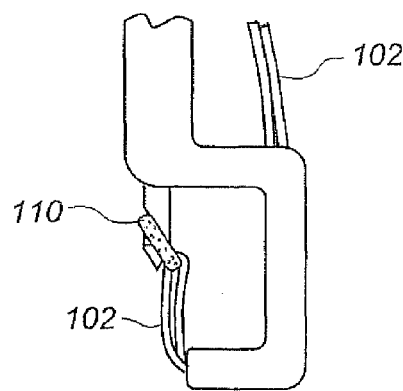
FIG. 1C is lateral view of the distal end of the embodiment of the invention drawn in FIG. 1A.

FIG. 1C is lateral view of the embodiment of the invention drawn in FIG. 1B with the needle partially retracted. The flexible handle component 110 was captured in the hook-like opening in the side of the needle. Retraction of the needle pulls the handle component and the flexible longitudinal fixation component through the releasable fastening feature at the end of the footplate. The arms of the flexible longitudinal fixation component are released from the handle of the instrument as the needle is retracted. The length of the opening in the handle component is preferably longer than the distance between the hook-like slot opening in the side of the needle and the tip of needle. As shown in FIG. 1C, the configuration permits the handle component to swivel past the distal tip of the needle. The handle component preferably bends, flexes, or deforms as it passes through the AF to avoid enlarging the hole in the AF. The handle component prevents inadvertently pulling the flexible longitudinal fixation component back into the IVD while removing the footplate from the IVD.

Figure 1D:
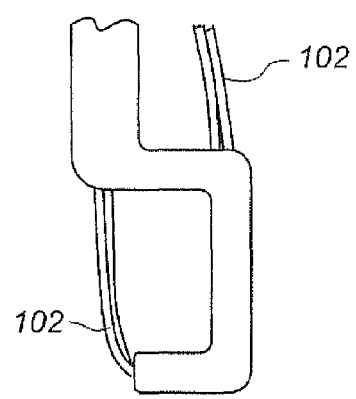
FIG. 1D is a second lateral view of the distal end of the embodiment of the invention drawn in FIG. 1A.

FIG. 1D is a lateral view of the embodiment of the invention drawn in FIG. 1C with the needle further retracted. The handle component of the flexible longitudinal component lies within the cannulated component of the instrument.

Figure 1E:
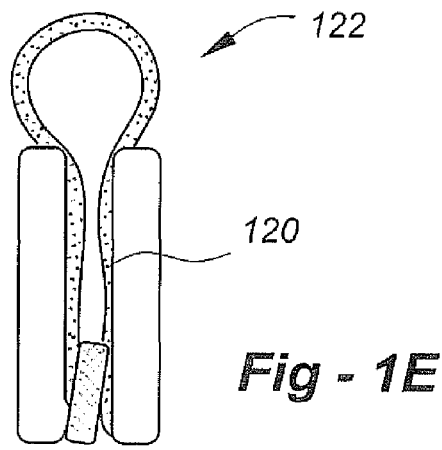
FIG. 1E is a view of the bottom of the footplate of the embodiment of the invention drawn in FIG. 1A.

FIG. 1E is view of the bottom of the footplate of the embodiment of the invention drawn in FIG. 1A. The proximal portion 120 of the handle component and of the flexible longitudinal fixation component is seen within the slot in the bottom of the footplate. The distal portion 122 of the handle component is seen extending beyond the distal end of the footplate. The handle component partially lies in a horizontal slot-like opening in the footplate. The handle component could lie over the footplate in alternative embodiments of the invention.

Figure 1F:
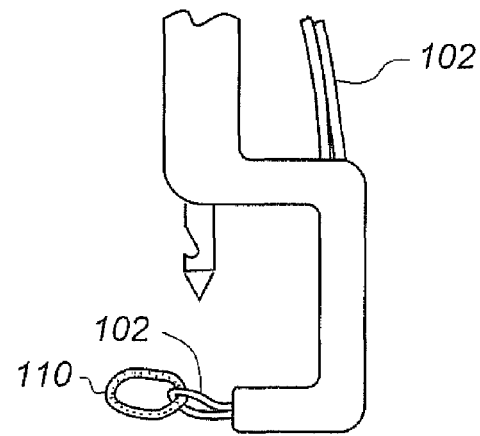
FIG. 1F is lateral view of the distal end of the embodiment of the invention drawn in FIG. 1A.

FIG. 1F is a lateral view of the distal end of the embodiment of the invention drawn in FIG. 1A. The handle component and the central portion of the flexible longitudinal fixation component are seen extending beyond the distal end of the footplate. The arms of the flexible longitudinal component are seen extending towards the handle of the instrument. Tension of the ends of the flexible longitudinal component pulls the handle component into the horizontal slot in the footplate. The circular shaped handle component is deformed into the shape shown in FIG. 1E as the handle component is pulled into the footplate. The handle component is preferably made of high tensile strength, flexible, elastic materials such as metal, nylon, or plastic. For example, the handle component could be made of steel, titanium, Nitinol, polyethylene, polypropylene, of other similar material. The handle component is preferably between 2 and 6 millimeters wide and between 2 and 10 millimeters long. Alternatively, the handle component may be 0.5, 1.0, 6.1, 6.2, 6.3, 6.4, 6.5, 6.6, or more than 6.6 millimeters wide or more than 10 millimeters long in alternative embodiments of the invention. The handle component is preferably made of material 0.1 to 2 millimeter in diameter. The handle component preferably has a tensile strength of 20 to 80 pounds. Alternatively, the handle component may have a tensile strength of more than 80 pounds. The handle component may have oval, rectangular, square, or other shapes in alternative embodiments of the invention. The handle component may be a hoop or a longitudinal element bent in a generally circular or other shape where the ends of the longitudinal component contact one another or are near one another to form a closed or almost closed component. For example, the handle component could be a solid ring or a wire coil like the component used in key rings.

Figure 1G:
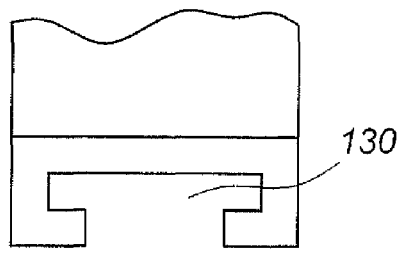
FIG. 1G is a view of the distal end of the footplate of the embodiment of the invention drawn in FIG. 1A.

FIG. 1G is view of the distal end of the footplate drawn in FIG. 1F. The handle component fits in the horizontal slot 130. The arms of flexible longitudinal fixation component pass through the vertical and horizontal slots. The handle component and flexible longitudinal component are loaded into the footplate by passing the arms of the flexible longitudinal component through the vertical slot into the horizontal slot then behind the footplate followed by pulling on the ends of the flexible longitudinal component to pull the handle component into the horizontal slot in the footplate. The horizontal slot is preferably 1 to 3 millimeters wide and 0.5 to 2 millimeters tall. Alternatively, the horizontal slot may be 0.5, 0.6, 0.7, 0.8, 0.9, 3.1, 3.2, 3.3, or more than 3.3 millimeters wide and 0.3, 0.4, 2.1, 2.2, 2.3, 2.4, 2.5, or more than 2.5 millimeters tall. The vertical slot is preferably 0.3 to 2.0 millimeters wide and 0.5 to 1.5 millimeters tall. Alternatively, the vertical slot could be 0.2, 2.1, 2.2, 2.3, 2.4, 2.5, 2.6, 2.7, or more than 2.7 millimeters wide and 0.3, 0.4, 1.6, 1.7, 1.8, 1.9, less than 0.3, or more than 1.9 millimeters tall.

Figure 1H:
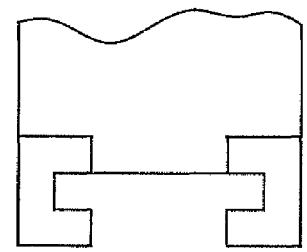
FIG. 1H is a view of the distal end of a footplate of an alternative embodiment of the invention drawn in FIG. 1G.

FIG. 1H is a view of the distal end of a footplate of an alternative embodiment of the invention drawn in FIG. 1G. The vertical slot passes through the top and the bottom of the footplate. The vertical slot is thus taller than the vertical slot drawn in FIG. 1G.

Figure 1I:
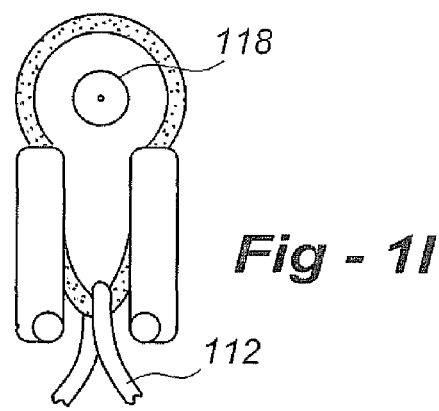
FIG. 1I is a view of the bottom of the footplate of an alternative embodiment of the invention drawn in FIG. 1E.

FIG. 1I is a view of the bottom of the footplate of an alternative embodiment of the invention drawn in FIG. 1E. The needle component and a portion of a flexible longitudinal fixation component are seen within the opening of the handle component. The end of a retractable stop component is seen adjacent to the proximal end of the handle component. The handle component is held in a horizontal slot of the footplate. Tension on the flexible longitudinal fixation component, whose ends are cleated in the handle of the instrument, holds the proximal end of the handle component against the retractable slot. Space is seen between all sides of the needle and the interior of the handle component. Such space is preferably 0.5 to 6.0 millimeters in all directions, but not necessarily the same distance in all directions. The length of such space is most preferably 1.0 to 3.0 millimeters in all directions.

Figure 1J:
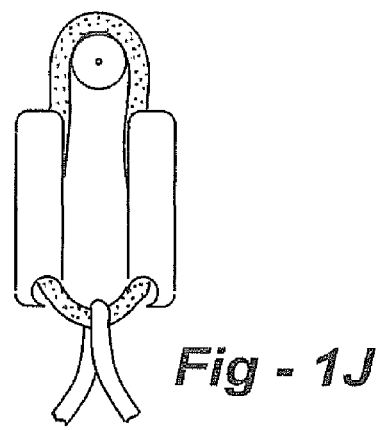
FIG. 1J is a view of the bottom of the footplate of the embodiment of the invention drawn in FIG. 1I.

FIG. 1J is a view of the bottom of the footplate drawn in FIG. 1I. The retractable stop component was retracted, which enabled the handle component to slide towards the flexible longitudinal fixation component. The ends of the flexible longitudinal fixation were uncleated from the handle of the instrument and pulled to slide the handle component against the side of the needle. Then the ends of the flexible longitudinal fixation component were recleated to maintain pressure between the handle component and the side of the needle.

Figure 1K:
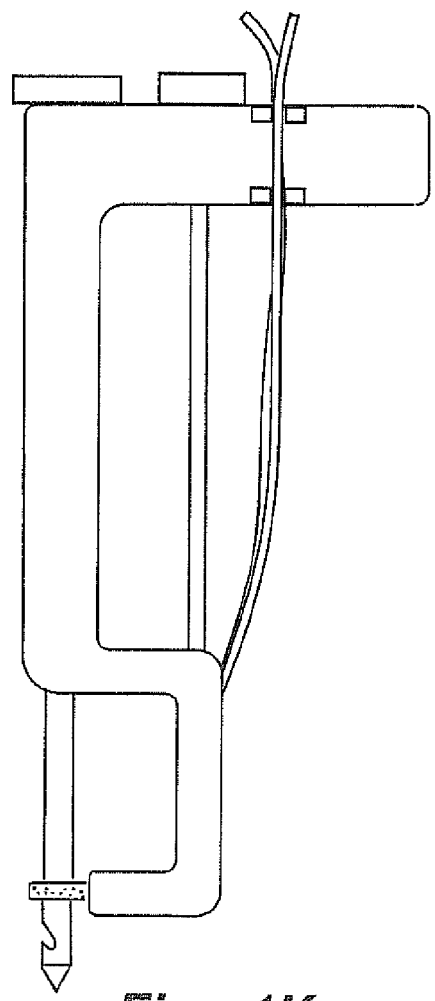
FIG. 1K is a lateral view of the embodiment of the invention drawn in FIG. 1I.

FIG. 1K is a lateral view of the embodiment of the invention drawn in FIG. 1I. The shaft of the retractable stop component is parallel to the shaft of the instrument. The hook-like opening in the side of the needle is seen beyond the handle component. The ends of the flexible longitudinal fixation component pass through first and second cleats on the handle of the instrument.

Figure 1L:
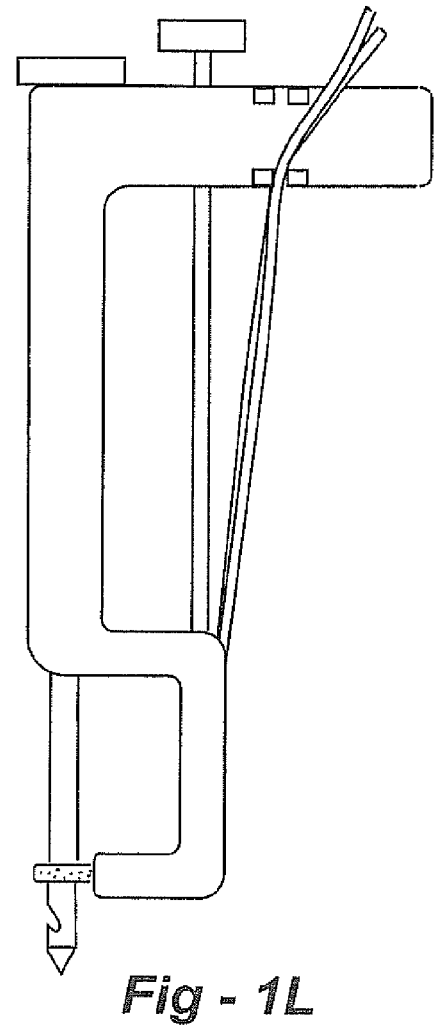
FIG. 1L is a lateral view of the embodiment of the invention drawn in FIG. 1J.

FIG. 1L is a lateral view of the embodiment of the invention drawn in FIG. 1J. The retractable stop component was retracted. The ends of the flexible longitudinal fixation component were released from the first cleat. Tension on the ends of the flexible longitudinal fixation component pulls the handle component to the side of the needle. The ends of the flexible longitudinal fixation are then passed into the first cleat to maintain tension on the flexible longitudinal fixation component. The needle is retracted to capture the handle component in the next step of the technique followed by release of the ends of the flexible longitudinal fixation component from the first cleat. The second cleat provides mild tension on the flexible longitudinal fixation component as the needle is retracted through tissue, which helps hold the handle component in the notch of the needle. The arms of the flexible longitudinal component slide through the second cleat.

The invention taught in FIGS. 1A and 1B requires precise placement of the needle relative to the handle component. In such invention, the side of the needle must contact the inside of the handle component and create tension on the handle component and the flexible longitudinal fixation component. The invention taught in FIGS. 1I-1L overcomes the requirement for precise needle placement relative to the handle component. In such preferred embodiment of the invention, the needle simply needs to pass through the opening in the handle component. The handle component is then moved to provide contact and tension between the inside of the handle component and the side of the needle.

Figure 1M:
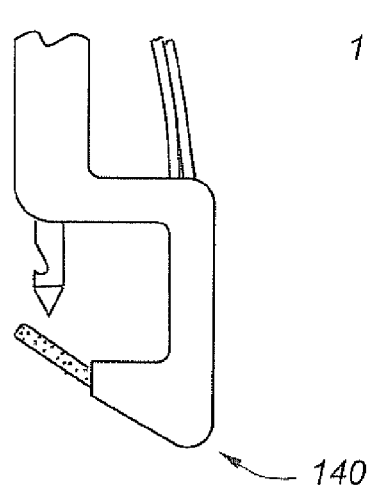
FIG. 1M is a lateral view of an alternative embodiment of the invention drawn in FIG. 1C.

FIG. 1M is a lateral view of an alternative embodiment of the invention drawn in FIG. 1C. The convex surface of the distal end of the footplate facilitates insertion of the footplate through apertures in the AF. The inclined handle component facilitates extraction of the handle and flexible longitudinal fixation components from the footplate by the needle component.

Figure 1N:
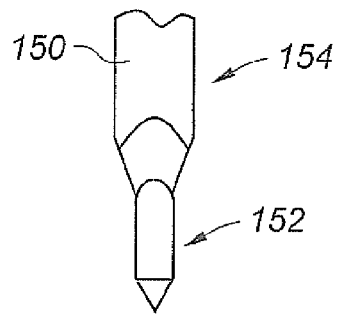
FIG. 1N is a lateral view of an alternative embodiment of the needle drawn in FIG. 1M.

FIG. 1N is a lateral view of an alternative embodiment of the needle-like component drawn in FIG. 1M. The distal end of the needle-like component is narrower than the proximal end of the needle-like component to allow a narrower handle component than used with wider needles. The narrow handle component facilitates pulling the handle through the aperture created through the AF by the wider proximal portion of the needle-like component. Flat surfaces along the sides of the distal end of the needle-like component allow handle component to swivel in the hook-like opening of the needle-like component.

Figure 1O:
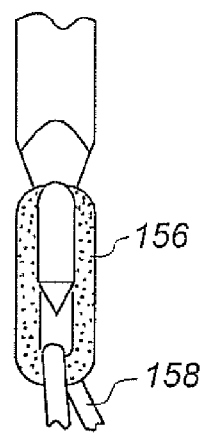
FIG. 1O is a lateral view of the needle drawn in FIG. 1N, a handle component and a portion of a flexible longitudinal fixation component.

FIG. 1O is a lateral view of the needle-like component drawn in FIG. 1N, a handle component and a portion of a flexible longitudinal fixation component. The handle component is captured in the hook-like portion of the needle-like component.

Figure 1P:
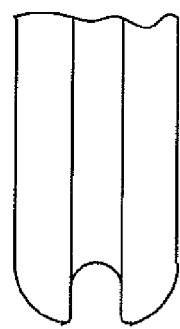
FIG. 1P is a posterior view of the embodiment of the invention drawn in FIG. 1M.

FIG. 1P is a posterior view of the embodiment of the invention drawn in FIG. 1M. The flexible longitudinal fixation is not included in the drawing. The convex surface of the distal end of the footplate facilitates insertion of the footplate through apertures in the AF.

Figure 1Q:
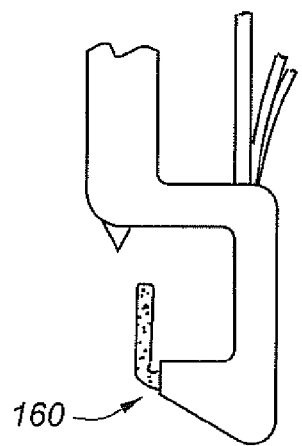
FIG. 1Q is a lateral view of an alternative embodiment of the invention drawn in FIG. 1M.

FIG. 1Q is a lateral view of the distal end of an alternative embodiment of the inventions drawn in FIGS. 1L & 1M. The handle component is hinged. Such hinge, which lies beyond the end of the footplate, enables bending of the hinge while the footplate is passed through an aperture in the AF. One or more hinge features preferably increase flexibility of the handle component in a generally vertical direction, toward or away from the handle of the instrument, without increasing flexibility of the handle component in a generally horizontal direction. Handle components made of shape memory materials, such as Nitinal, could be used to facilitate bending of the handle component toward or away from the handle of the instrument in situ.

Figure 1R:
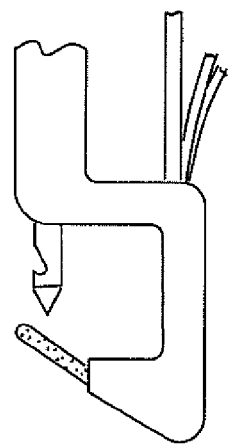
FIG. 1R is a lateral view of the embodiment of the invention drawn in FIG. 1Q.

FIG. 1R is a lateral view of the embodiment of the invention drawn in FIG. 1Q. Tension on the ends of the flexible longitudinal fixation component pulls the hinged portion of the handle component inside the footplate, which increases the stiffness of the exposed portion of the handle component and aligns the handle component with the footplate. The proximal end of the handle component is pulled against the retractable component as shown in FIG. 1I. The needle then captures the handle component as shown in FIGS. 1I-1L.

Figure 2A:
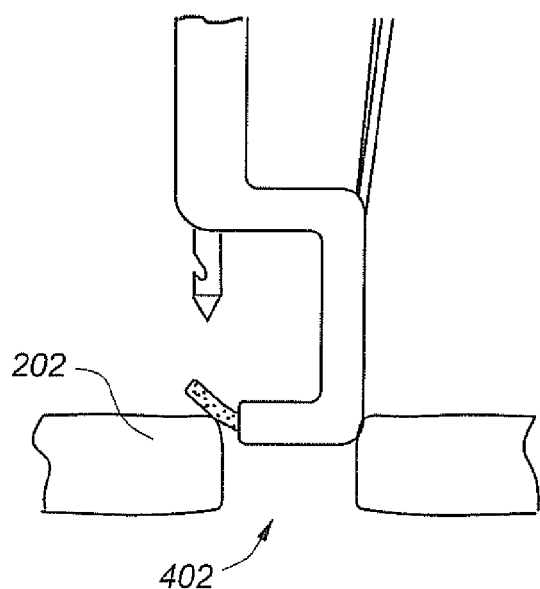
FIG. 2A is a lateral view of the distal end of the embodiment of the invention drawn in FIG. 1A and a cross section of a portion of the AF.

FIG. 2A is a superior view of an axial cross section of a portion of the AF 202 and a lateral view of the embodiment of the invention drawn in FIG. 1A. The footplate of the invention drawn in FIG. 1A was placed into an aperture 402 in the AF. The flexible handle component bends to facilitate passing the footplate through the aperture. The AF is stiffer than the nucleus pulposus (NP). The handle component is preferably flexible enough to bend when forced through and aperture in the AF, but stiff enough to resist bending when the component is moved through the NP. The handle component is also stiff enough to remain in the slot of the footplate as the exposed portion of the handle is manipulated in tissue.

Figure 2B:
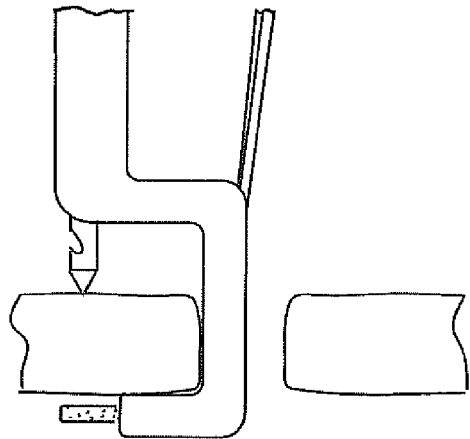
FIG. 2B is a second lateral view of the distal end of the embodiment of the invention in FIG. 1A and a cross section of a portion of the AF.

FIG. 2B is a superior view of an axial cross section of a portion of the AF and a lateral view of the embodiment of the invention drawn in FIG. 2A. The footplate is generally rotated 90 degrees and pressed against the inner portion of the AF. The portion of the handle component that extends beyond the footplate is preferably stiff enough to dissect and pass through nucleus tissue. Alternatively, a right angled instrument could be used to create a space between the AF and the NP for placement of the footplate and the handle component. The handle component returns to its position parallel to the footplate after the footplate is passed through the aperture. The tip of needle of the instrument is advanced through the AF and through the opening in the handle component in the next step in the method. The taper tip of the needle preferably separates rather cuts the fibers of the AF.

Figure 3A:
FIG. 3A is a lateral view of the flexible longitudinal fixation component and intra-aperture component drawn in FIG. 1A.

FIG. 3A is lateral view of the handle, flexible longitudinal fixation, and intra-aperture components drawn in FIG. 1A. The ends of the flexible longitudinal fixation component pass through the center of the generally circular shaped intra-aperture component. The intra-aperture component is preferably 2 to 10 millimeters in diameter and 1 to 4 millimeters thick. The intra-aperture component is preferably made of polyester mesh, polypropylene mesh, or autograft or allograft tissue such as fascia, tendon, ligaments, or AF. The ends of the flexible longitudinal component are preferably passed through the locking mechanism of a suture anchor.

Figure 3B:
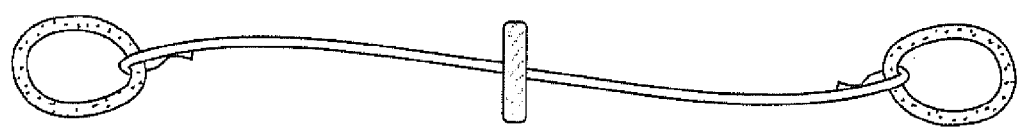
FIG. 3B is a lateral view of an alternative embodiment of the invention drawn in FIG. 3A.

FIG. 3B is a lateral view of an alternative embodiment of the invention drawn in FIG. 3A. An arm of a flexible longitudinal fixation component was through the intra-aperture component. The arms of the flexible longitudinal then passed through handle components and welded to more central portions of the flexible longitudinal components. For example, thermal or ultrasonic welders by Tornier (Edina, Minn.) may be used to weld braided polyester suture and nylon suture flexible longitudinal fixation components respectively. The sutures are preferably USP #2 in size. Alternative suture material, suture size, and suture fastening mechanisms could be used in alternative embodiments of the invention.

Figure 3C:
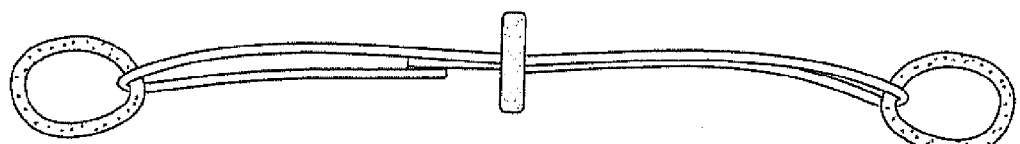
FIG. 3C is a lateral view of an alternative embodiment of the invention drawn in FIG. 3B.

FIG. 3C is a lateral view of an alternative embodiment of the invention drawn in FIG. 3B. The first arm of the flexible longitudinal fixation was passed through the intra-aperture component then through a first handle component then through the intra-aperture component. The second arm of the flexible longitudinal fixation component was passed through a second handle component then welded, or otherwise fastened, to the distal end of the first arm of the flexible longitudinal fixation component.

Figure 4A:
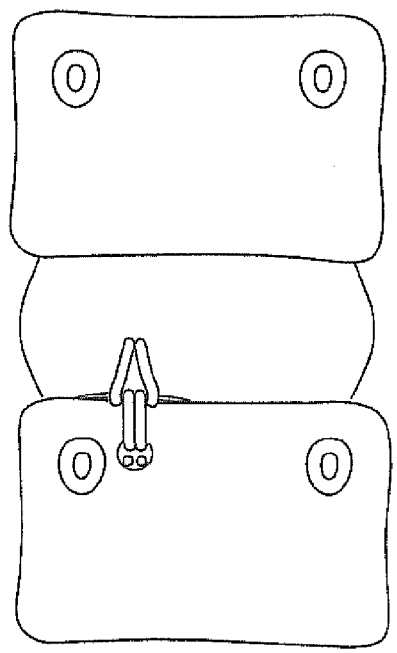
FIG. 4A is a posterior view of a coronal cross section of a portion of the spine and the embodiment of the invention drawn in FIG. 3A.

FIG. 4A is a posterior view of a coronal cross section of a portion of the spine and the embodiment of the invention drawn in FIG. 3A. The invention drawn in FIG. 1A was used to pass the central portion of the flexible longitudinal fixation component through AF tissue above an aperture near the caudal vertebral body. The handle component was cut and discarded after the central, loop, portion of the flexible longitudinal fixation component was pulled through the AF. One arm of the flexible longitudinal fixation could be held while pulling the end of the second arm of such component. Such invention enables removal of the portion of the flexible longitudinal fixation component that was looped over the handle, which could damage such portion of the flexible fixation component, to be cut are discarded later in the procedure. The device was then fastened to the spine using the method taught in FIGS. 7A-E of my co-pending application PCT/US2009/065954.

Figure 4B:
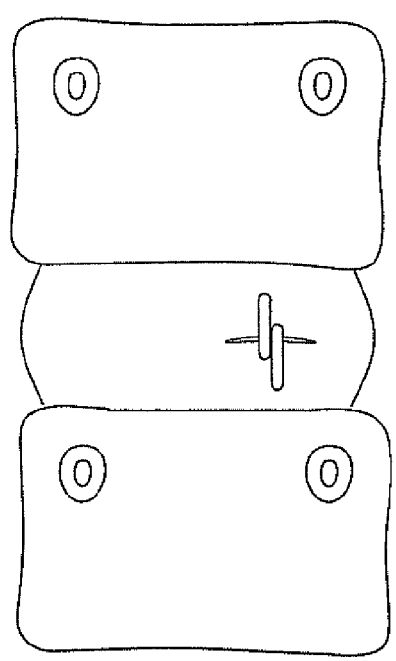
FIG. 4B is a posterior view of a coronal cross section of a portion of the spine and the embodiment of the invention drawn in FIG. 3B.

FIG. 4B is a posterior view of a coronal cross section of a portion of the spine and the embodiment of the invention drawn in FIG. 3B. The invention drawn in FIG. 1A was used to pass the first arm of the flexible longitudinal fixation component through AF tissue above the aperture and the second arm of the flexible longitudinal fixation component through AF tissue below the aperture. The ends of the flexible longitudinal fixation components were cut proximal to the handle components and the handle components were discarded. The ends of the flexible longitudinal fixation components were welded together after the intra-aperture component was placed into the aperture as taught in FIGS. 4A-J of my co-pending application PCT/US2009/065954.

FIG. 4C is a posterior view of a coronal cross section of a portion of the spine and the embodiment of the invention drawn in FIG. 3C. The invention drawn in FIG. 1A was used to pass the first arm of the flexible longitudinal fixation component through AF tissue to the left of the aperture and the second arm of the flexible longitudinal fixation component through AF tissue to the right of the aperture. The ends of the flexible longitudinal fixation components were cut proximal to the handle components and the handle components were discarded. The ends of the flexible longitudinal fixation components were welded together after the intra-aperture component was placed into the aperture as taught in FIGS. 6A-D of my co-pending application PCT/US2009/065954.

FIG. 5A is a lateral view of the distal end of an alternative embodiment of the invention drawn in FIG. 1A. The distal end of the footplate extends to the distal end, or near the distal end of the flexible handle component. FIG. 5B is lateral view of the embodiment of the invention drawn in FIG. 5A.

FIG. 6A is a lateral view of the distal end of an alternative embodiment of the invention drawn in FIG. 5A. The opening in the side of the needle component faces the side of the footplate. The handle component is seen in an opening in the side of the footplate. FIG. 6B is a lateral view of the embodiment of the invention drawn in FIG. 6A. The distal end of the footplate extends of the distal end, or near the distal end of the flexible handle component.

FIG. 7A is lateral view of an alternative embodiment of the handle component drawn in FIG. 3B. A U-shaped handle component was fastened to the end of a flexible longitudinal fixation component. For example, a flexible longitudinal component could be wrapped around the arms of the U-shaped handle component and the end of the flexible longitudinal fixation component. Alternative methods or devices could be used to fasten U-shaped handle components to the ends of flexible longitudinal fixation components in alternative embodiments of the invention.

FIG. 7B is a lateral view of an alternative embodiment of the handle component drawn in FIG. 7A. A component with generally circular opening was fastened to the end of a flexible longitudinal fixation component. For example the proximal end of the handle component could be crimped, swaged, or swedged on to the end of the flexible longitudinal fixation component.

FIG. 8A is lateral view of an alternative embodiment of the invention drawn in FIG. 3B. A first end of looped shaped component was passed through an intra-aperture component. The arms of the looped shaped component were preferably fastened together. For example, the arms of a nylon looped shaped component could be welded together. FIG. 8B is a lateral view of the embodiment of the invention drawn in FIG. 8A. The end of a flexible longitudinal fixation component was passed through the opening in the looped shaped component. FIG. 8C is an exploded lateral view of the embodiment of the invention drawn in FIG. 8B. The looped shaped component was pulled through the intra-aperture component to pull the flexible longitudinal fixation component through the intra-aperture component.

FIG. 8D is a lateral view of the embodiment of the invention drawn in FIG. 8C. The ends of the flexible longitudinal fixation component were passed through openings in handle components and welded to more central portions of the flexible longitudinal fixation component. The method taught in FIGS. 8A-D, enable surgeons to assemble such device during surgery. The assembled device cooperates with the invention drawn in FIG. 1A. Alternatively, the inventions drawn in FIGS. 3A-3C could be fully assembled during manufacturing and the fully assembled devices supplied to hospitals.

FIG. 9A is a lateral view of an alternative embodiment of the invention drawn in FIG. 1A. The handle of the flexible longitudinal fixation component lies within the footplate.

FIG. 9B is a lateral view of the embodiment of the invention drawn in FIG. 9A. A rod-like actuator was advanced in the distal portion of the instrument thereby pushing the distal end of the handle of the flexible longitudinal fixation component beyond the end of the footplate.

Figure 9C:
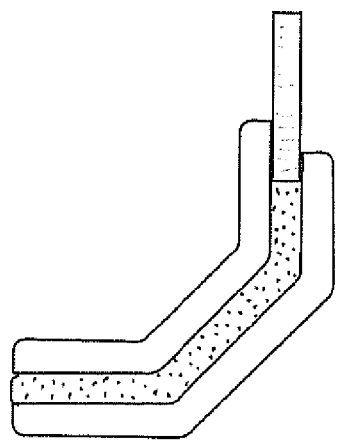
FIG. 9C is a lateral view of a longitudinal cross section of the distal end of the embodiment of the invention drawn in FIG. 9A.

FIG. 9C is a lateral view of a longitudinal cross section of the distal end of the instrument drawn in FIG. 9A. The retracted position of the handle component facilitates insertion of the footplate through apertures in the AF. The proximal end of the handle component may be more flexible than the distal end of such component. The flexible proximal end of the handle component facilitates bending of the component as it is advanced around curved or angled areas of the footplate.

Figure 9D:
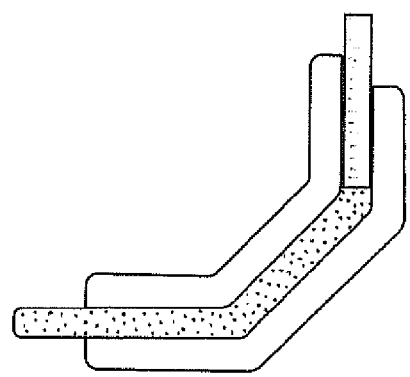
FIG. 9D is a lateral view of a longitudinal cross section of the distal end of the embodiment of the invention drawn in FIG. 9A.

FIG. 9D is a lateral view of a longitudinal cross section of the distal end of the instrument drawn in FIG. 9B. The handle component is pushed beyond the tip of the footplate after the footplate is placed through the aperture in the AF.

Figure 9E:
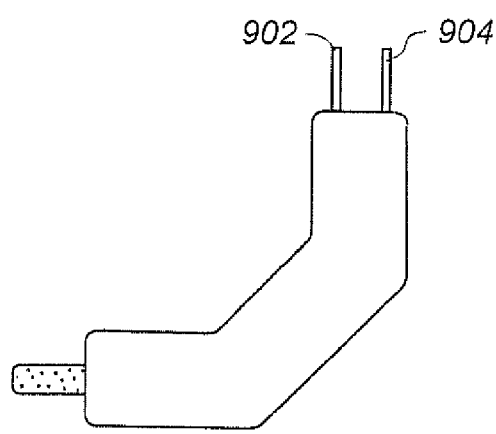
FIG. 9E is a lateral view of a footplate of an alternative embodiment of the invention drawn in FIG. 9A.

FIG. 9E is a lateral view of the footplate of an alternative embodiment of the invention drawn in FIG. 9A. Retractable, actuators are seen at the top of the drawing. The handle component extends from the tip of the footplate.

Figure 9F:
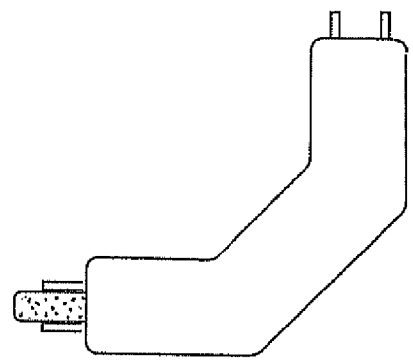
FIG. 9F is a lateral view of the embodiment of the invention drawn in FIG. 9E.

FIG. 9F is lateral view of the embodiment of the invention drawn in FIG. 9E. The retractable components were advanced above and below the handle component. The retractable components are generally advanced after the footplate is passed behind the inner layer of the AF. The retractable components align and hold the handle component in the desired position for capture by the needle. The retractable components could be limited to the area above or below the handle component in alternative embodiments of the invention.

Figure 9G:
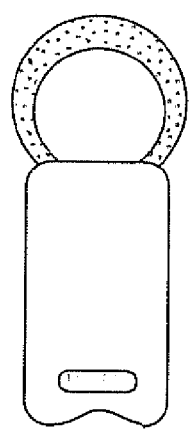
FIG. 9G is a superior view of the footplate drawn in FIG. 9E.
Figure 9H:
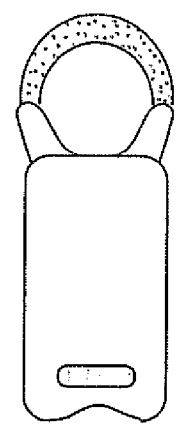
FIG. 9H is a superior view of the footplate drawn in FIG. 9F.

FIG. 9G is a superior view of the footplate drawn in FIG. 9E. FIG. 9H is a superior view of the footplate drawn in FIG. 9F. The retractable component was extended over portions of the handle component.

Figures 10A, 10B:
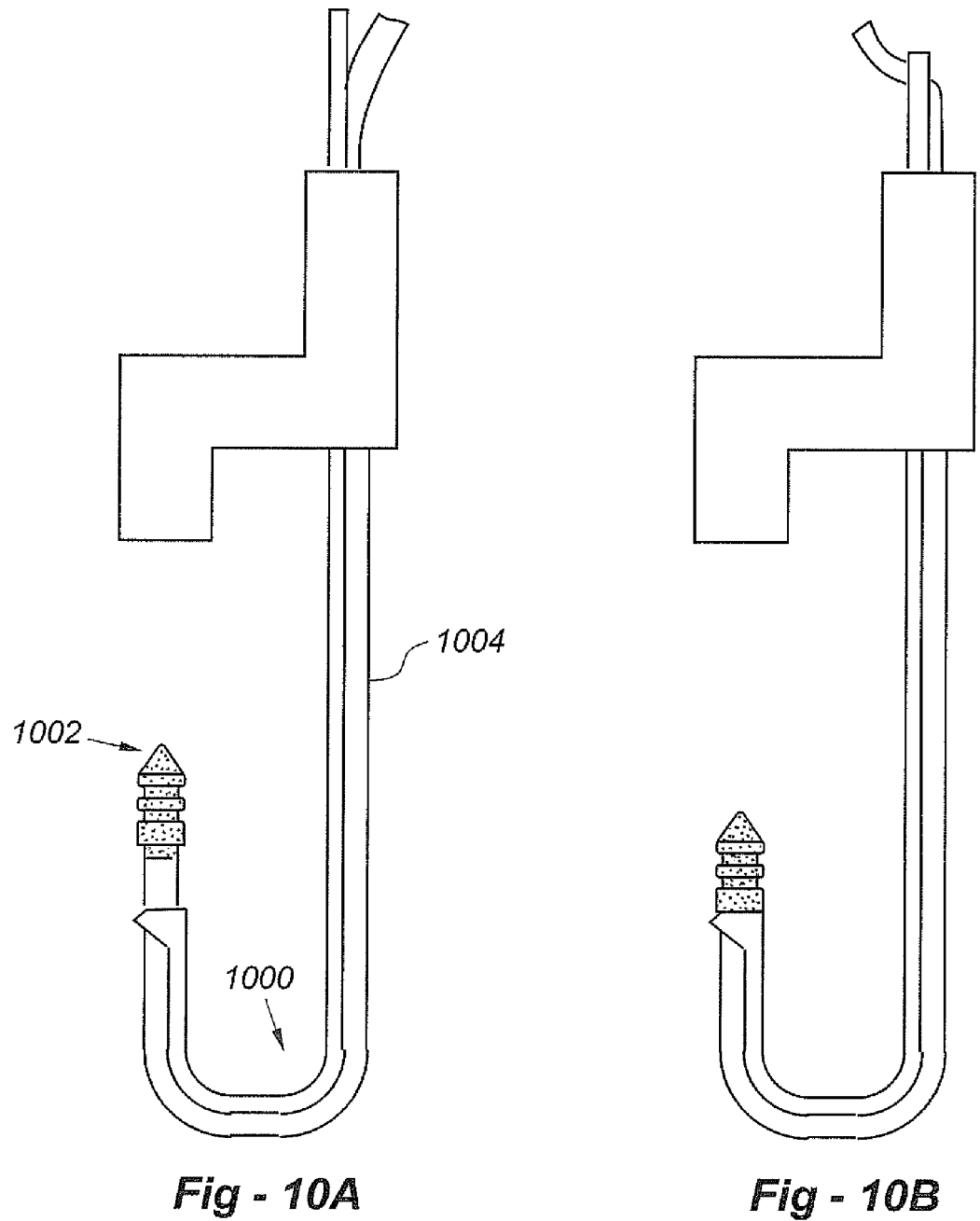
FIG. 10A is a lateral view of an alternative embodiment of the invention drawn in FIG. 1A.
FIG. 10B is a lateral view of the embodiment of the invention drawn in FIG. 10A.

FIG. 10A is a lateral view of an alternative embodiment of the invention drawn in FIG. 1A. A J-shaped needle holder holds the ribbed needle attached to the end of a flexible longitudinal fixation component. The shaft of the J-shaped needle holder and the flexible longitudinal fixation component pass through a cannulated component.

FIG. 10B is a lateral view of the embodiment of the invention drawn in FIG. 10A. Tension on the distal portion of the flexible longitudinal fixation component pulled the proximal end of the ribbed needle into the distal end of the needle holder. The distal portion of the flexible longitudinal fixation component was forced into a slit-like opening in the proximal portion of the needle holder. Tension on the flexible longitudinal fixation component holds the needle in the needle holder. The needle could be press fit into the needle holder, glued, welded or otherwise attached to the needle holder in alternative embodiments of the invention. Alternatively, the ribbed shaped tip of the needle could be broken from the J-shaped portion of the needle holder to release the ribbed shaped tip in alternative embodiments of the invention. The sides of the ribbed needle may have one or more flat surfaces that cooperate with the flat sides of a tool used to rotate the tip of the needle to break the tip of the needle.

Figure 10C:
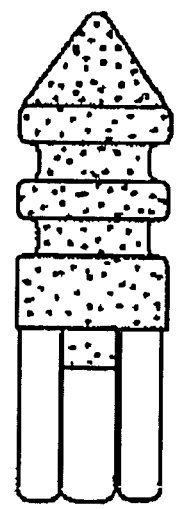
FIG. 10C is a lateral view of the distal end of the embodiment of the invention drawn in FIG. 10B.
Figure 10D:
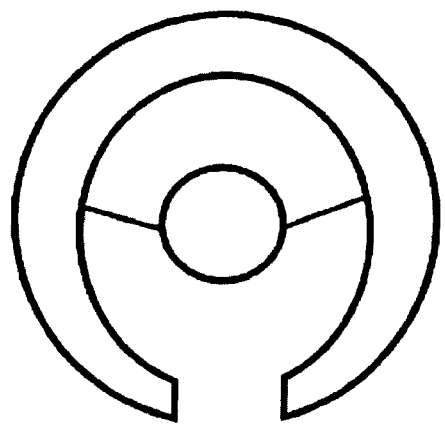
FIG. 10D is a superior view of a transverse cross section of the embodiment of the invention drawn in FIG. 10B.

FIG. 10C is lateral view of the distal end of the embodiment of the invention drawn in FIG. 10A. The flexible longitudinal fixation component fits through the slot in the distal end of the needle holder. FIG. 10D is superior view of a transverse cross section of the cannulated component. The flexible longitudinal fixation component is seen in the center of the assembled device. The flexible longitudinal fixation component sits in a recess in the needle holder. The flexible longitudinal fixation component fits through the slot in the cannulated component.

Figure 11A:
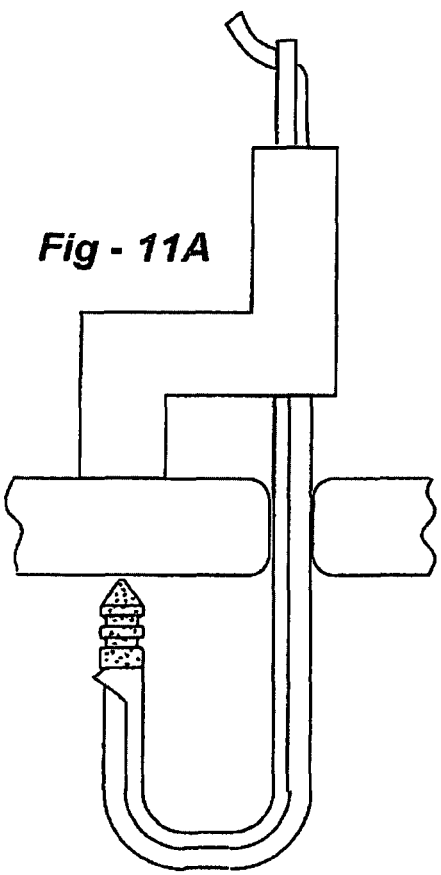
FIG. 11A is a lateral view of the embodiment of the invention drawn in FIG. 10B and a cross section of a portion of the AF.

FIG. 11A is a lateral view of the embodiment of the invention drawn in FIG. 10A and a cross section of a portion of the AF. The needle and the J-shaped portion of the needle were passed through an aperture in the AF and generally rotated approximately ninety degrees.

Figure 11C:
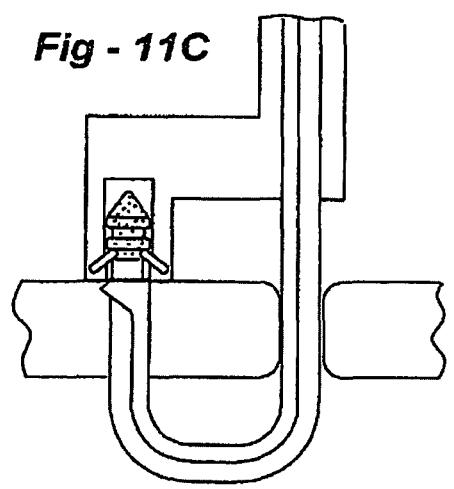
FIG. 11C is a lateral view of a longitudinal cross section of the embodiment of the invention drawn in FIG. 11B and a cross section of the AF.
Figure 11B:
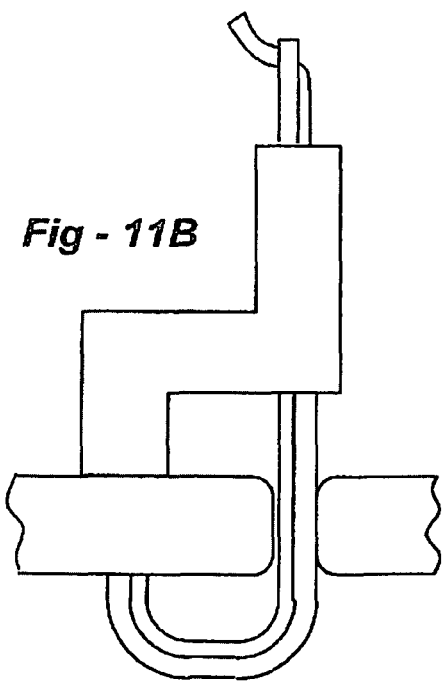
FIG. 11B is a lateral view of the embodiment of the invention drawn in FIG. 11A and a cross section of a portion of the AF.

FIG. 11B is a lateral view of the embodiment of the invention drawn in FIG. 11A and a cross section of a portion of the AF. The shaft of the needle holder was pulled through the cannulated component to advance the tip of the needle through the AF. The distal end of the cannulated component applies counter pressure on the AF.

FIG. 11C is a lateral view of a longitudinal cross section of the embodiment of the invention drawn in FIG. 11B and a portion of the AF. The needle was advanced into an opening in the distal end of the cannulated component. Elastic projections from the walls in the opening in the distal end of the cannulated component fit into recesses on the side of the needle. The distal end of the cannulated component protects nerves from the tip of the needle.

Figure 11D:
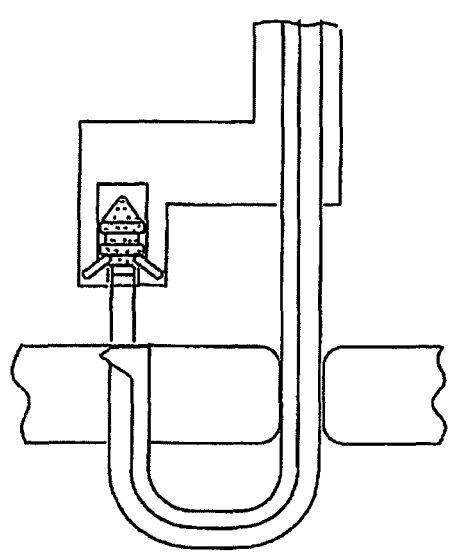
FIG. 11D is a lateral view of a longitudinal cross section of the embodiment of the invention drawn in FIG. 11B and a cross section of the AF.

FIG. 11D is a lateral view of a longitudinal cross section of the embodiment of the invention drawn in FIG. 11C and a portion of the AF. The cannulated component was pulled towards the proximal end of the needle holder, which pulls the distal end of the flexible longitudinal fixation component through the AF. The distal end of the flexible longitudinal fixation component is cut to release the needle and the cannulated component. The flexible longitudinal fixation component fits through the slot in the side of the cannulated component. The J-shaped needle holder is rotated ninety degrees and pulled through the aperture in the AF. The second end of the flexible longitudinal fixation component could be passed through AF tissue on the opposite side of the aperture in a similar manner in the next step of the procedure. The J-shaped needle is preferably made of a relatively stiff material such as steel. The shaft of the 7-shaped needle holder is preferably 1 to 3 millimeters in diameter. The needle holder is preferably 3 to 12 millimeters wide and 20 to 40 millimeters long.

FIG. 12A is lateral view of the distal end of an alternative embodiment of the invention drawn in FIG. 11A and a portion of the AF. The tip of a needle is seen extending from the distal end of the needle holder, which lies in a cannulated component.

FIG. 12B is a lateral view of the distal end of the embodiment of the invention drawn in FIG. 12A and a portion of the AF. The needle and the distal end of the needle holder were advanced through the cannulated component, which allows the distal end of the needle to assume a J-shape. The proximal end of the needle holder was pulled to force the needle through the AF. The J-shaped needle holder is preferably made of shape memory material such as Nitinol. The dimensions of the needle holder are described in the text of FIG. 11D. The cannulated component is preferably made of steel or other metal. The cannulated component is preferably 2 to 8 millimeters in diameter and 15 to 40 millimeters long. The cannulated component may be passed through an aperture in the AF or passed through AF tissue adjacent to the aperture. If passed through tissue lateral to the aperture, the invention facilitates passage of the needle from through the AF in an outside to inside direction on a first side of the aperture then an inside to outside direction through the AF tissue on the opposite side of the aperture.

FIG. 12C is an exploded lateral view of the embodiment of the invention drawn in FIG. 12B and a portion of the AF. The needle holder was pulled through the cannulated component, which straightens the J-shaped end of the needle holder. The needle holder assumes the J-shape after the needle holder is pulled from the cannulated component. The needle is grasped with an instrument or the cannulated component drawn in FIG. 11C to pull the flexible longitudinal component through the AF. The flexible longitudinal fixation component fits through a slot in the cannulated component. The cannulated component is pulled from the AF and the flexible longitudinal fixation component in the next step of the technique. The second end of the flexible longitudinal fixation component could be passed through AF tissue on the opposite side of the aperture using a similar method.

FIG. 12D is a superior view of a transverse cross section of the cannulated component drawn in FIG. 12B. The flexible longitudinal fixation component lies in a recess in the needle holder. The needle holder and the flexible longitudinal fixation component lie within the cannulated component. A second releasable component with a recess could be slid between the flexible longitudinal fixation component and the wall of cannulated component in an alternative component. Such second releasable component prevents the needle holder or the flexible longitudinal fixation component from migrating through the slot in the cannulated component prematurely.

Figure 13A:
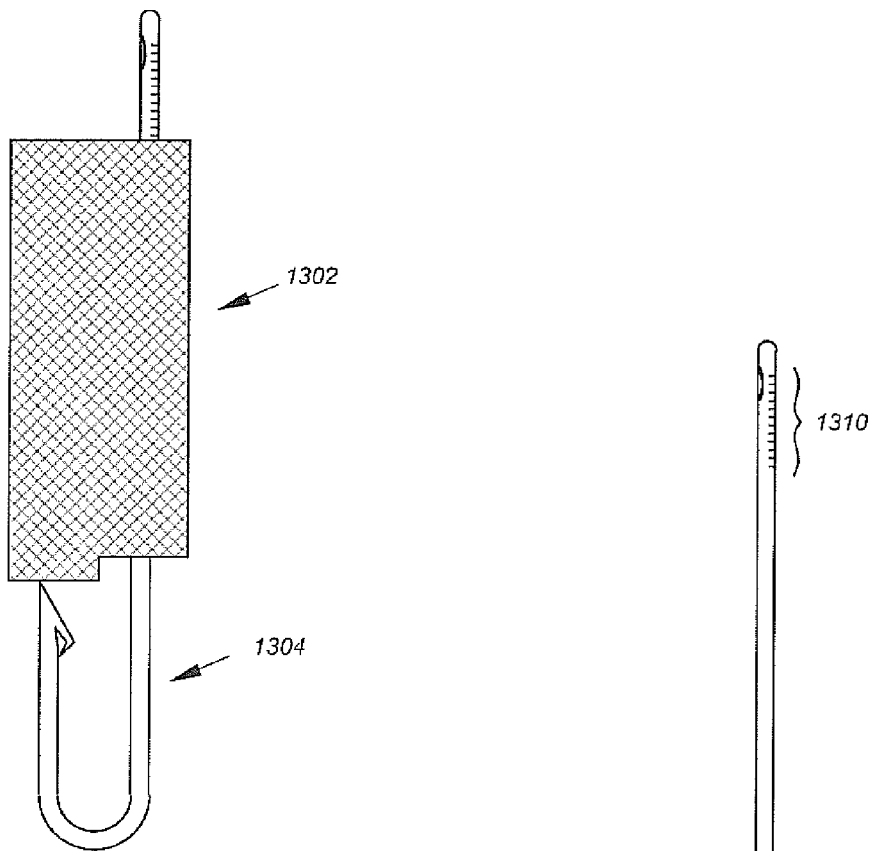
FIG. 13A is a lateral view of an alternative embodiment of the invention drawn in FIG. 11A.

FIG. 13A is a lateral view of an alternative embodiment of the invention drawn in FIG. 11A. A cannulated component was passed over the shaft of J-shaped needle. The J-shaped needle is preferably 2 to 8 millimeters wide and 20 to 40 millimeters long. The distal end of the J-shaped needle is preferably 5 to 15 millimeters long. The needle is preferably made of metal such as steel, titanium, or Nitinol.

Figure 13B:
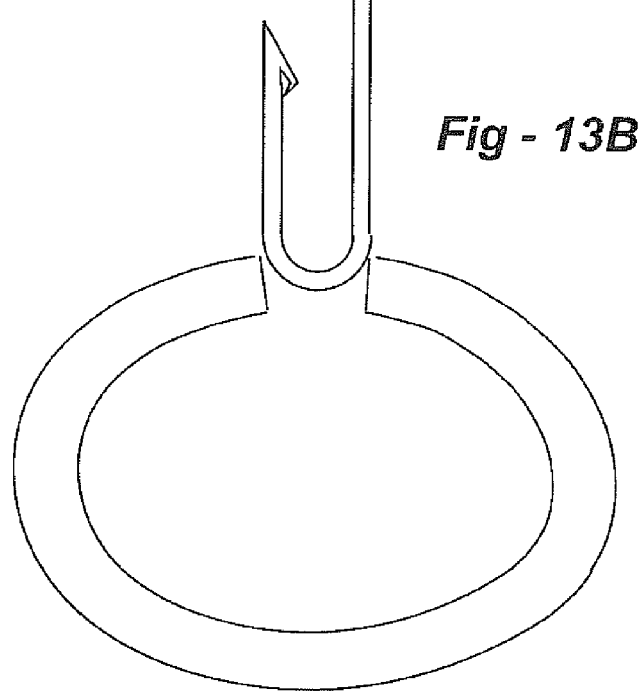
FIG. 13B is a lateral view of the embodiment of the invention drawn in FIG. 13A and a superior view of an axial cross section of the AF.

FIG. 13B is a lateral view of the embodiment of the invention drawn in FIG. 13A and a superior view of a cross section of an IVD. The distal end of needle lies over an aperture in the AF. Markings on the proximal end of the needle indicate which direction the distal end of the needle faces and cooperate with the cannulated component of determine the length of the needle below the cannulated component.

Figure 13C:
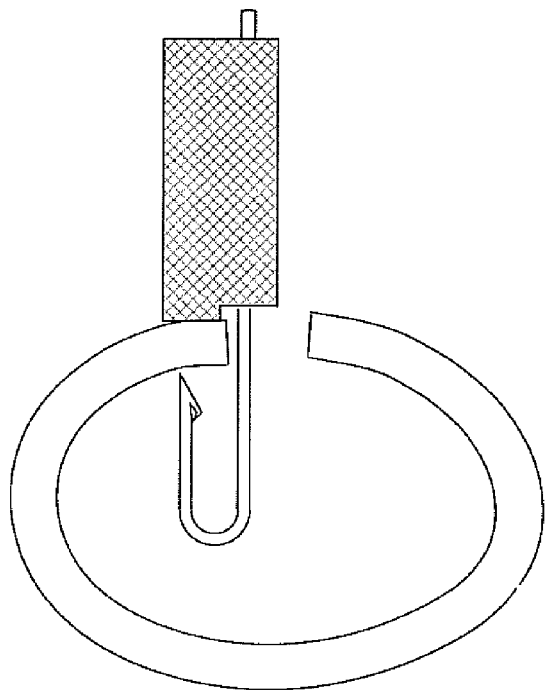
FIG. 13C is a lateral view of the embodiment of the invention drawn in FIG. 13B and a superior view of an axial cross section of the AF.

FIG. 13C is a lateral view of the embodiment of the invention drawn in FIG. 13B and a superior view of a cross section of an IVD. The distal end of the needle was pushed through the aperture and generally rotated about ninety degrees. The cannulated component was pushed onto the IVD to apply counter pressure and protect the nerves from the tip of the needle.

Figure 13D:
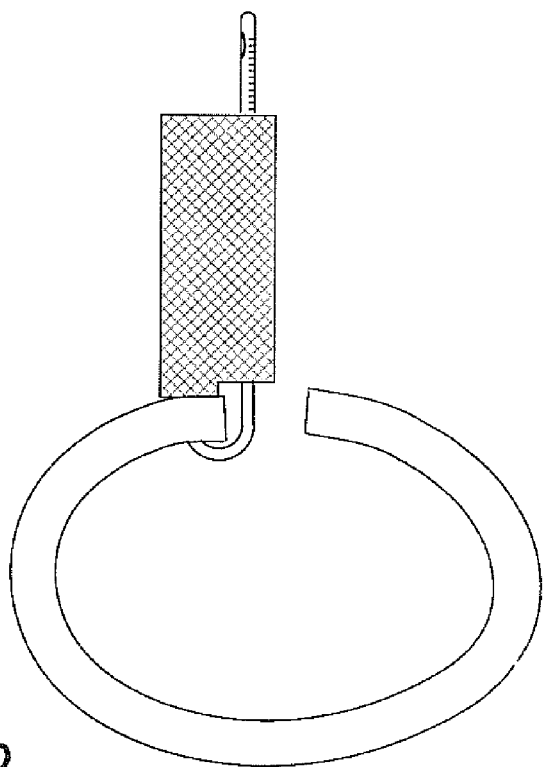
FIG. 13D is a lateral view of the embodiment of the invention drawn in FIG. 13C and a superior view of an axial cross section of the AF.

FIG. 13D is a lateral view of the embodiment of the invention drawn in FIG. 13C and a superior view of a cross section of an IVD. Tension on the proximal end of the needle pulled the distal end of the needle through the AF and into an opening in the cannulated component.

Figure 13E:
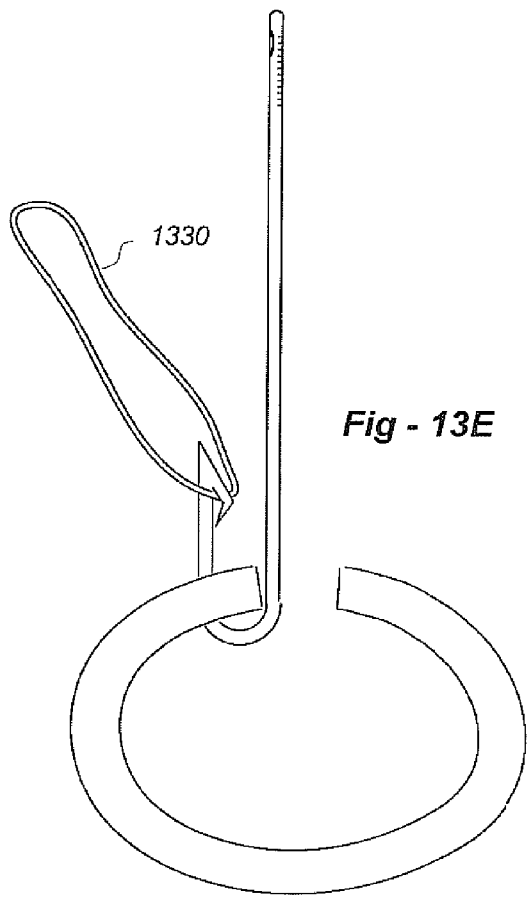
FIG. 13E is a lateral view of the embodiment of the invention drawn in FIG. 13D and a superior view of an axial cross section of the AF.

FIG. 13E is a lateral view of the embodiment of the invention drawn in FIG. 13D and a superior view of a cross section of an IVD. The cannulated component was pulled over the proximal end of the needle and removed. A wire loop was pulled through the opening near the distal end of the needle.

Figure 13F:
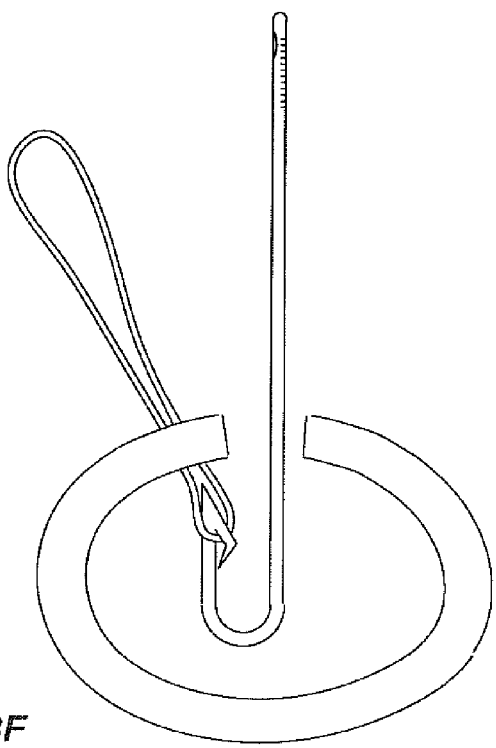
FIG. 13F is a lateral view of the embodiment of the invention drawn in FIG. 13E and a superior view of an axial cross section of the AF.

FIG. 13F is a lateral view of the embodiment of the invention drawn in FIG. 13D and a superior view of a cross section of an IVD. The distal end of the needle was pushed into the IVD, which pulled one end of the wire loop into the IVD. The shape of the tip of the needle facilitates pulling the needle through the AF in inside to outside and outside to inside directions.

Figure 13G:
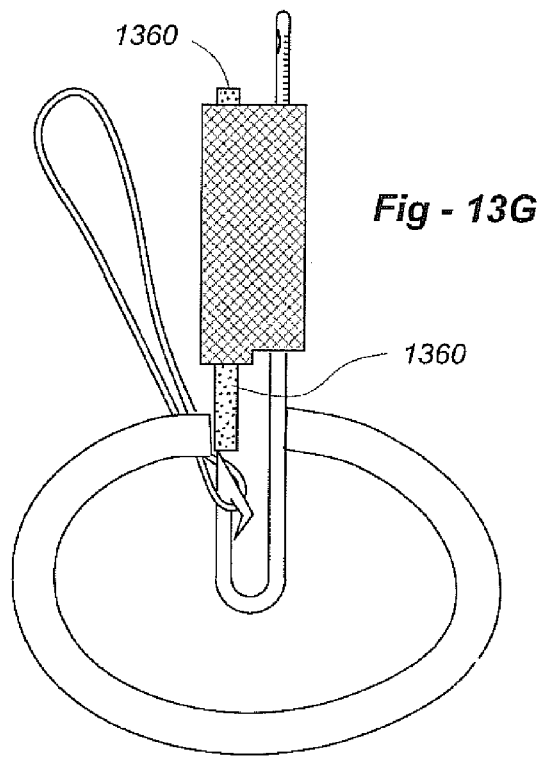
FIG. 13G is a lateral view of the embodiment of the invention drawn in FIG. 13F and a superior view of an axial cross section of the AF.

FIG. 13G is a lateral view of the embodiment of the invention drawn in FIG. 13F and a superior view of a cross section of an IVD. A cannulated component was passed over the shaft of the needle. A rod component was advanced through an opening in the cannulated component, through the aperture, and over the pointed tip of the needle to prevent the tip of needle from contacting the AF during withdraw of the needle from the IVD. The tip of a needle made of shape memory material could move towards the shaft of the needle, when heated by the disc, in an alternative embodiment of the invention to facilitate passing the needle through the aperture as the needle is withdrawn from the IVD.

Figure 13H:
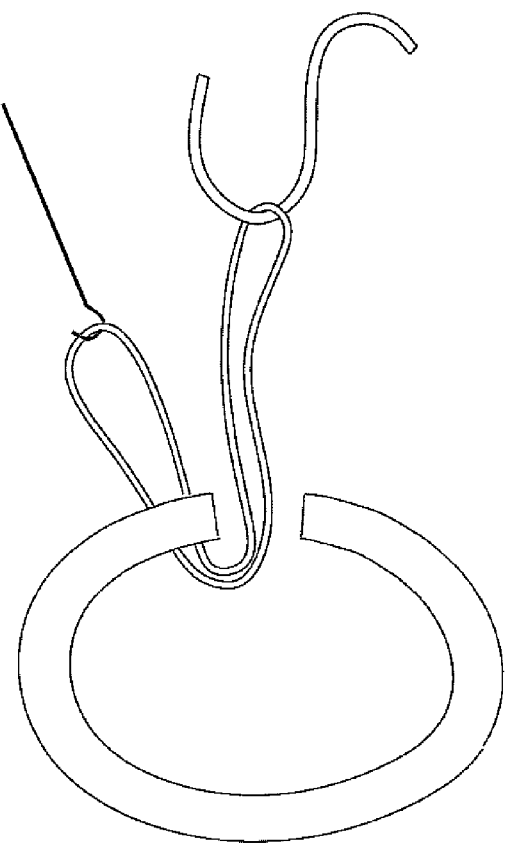
FIG. 13H is a lateral view of the embodiment of the invention drawn in FIG. 13G and a superior view of an axial cross section of the AF.

FIG. 13H is a lateral view of the embodiment of the invention drawn in FIG. 13G and a superior view of a cross section of an IVD. The needle was removed from the IVD pulling the first end of the wire loop through the aperture. The wire loop was pulled from the needle and needle was removed. The end of a flexible longitudinal fixation component was passed through the opening in the first end of the wire loop. The hook of an instrument was passed through the second end of the wire loop.

Figure 13I:
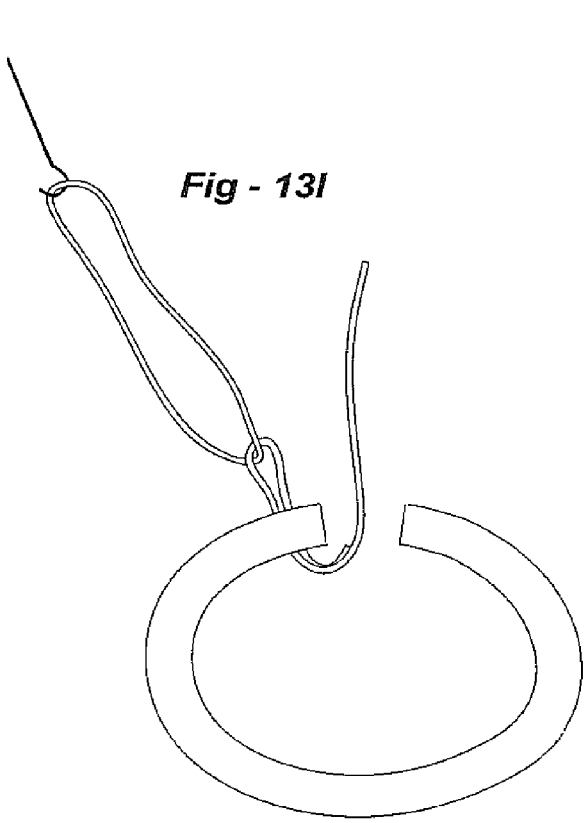
FIG. 13I is a lateral view of the embodiment of the invention drawn in FIG. 13H and a superior view of an axial cross section of the AF.
Figure 13J:
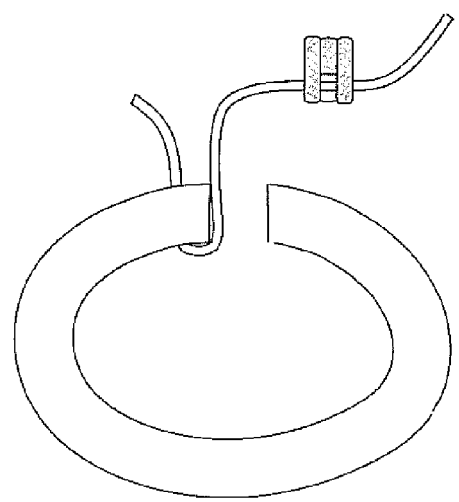
FIG. 13J is lateral view of the embodiment of the invention drawn in FIG. 13I and a superior view of an axial cross section of the AF.

FIG. 13I is a lateral view of the embodiment of the invention drawn in FIG. 13H and a superior view of a cross section of an IVD. Tension on the wire loop pulls the end of the flexible longitudinal fixation component through the AF. FIG. 13J is a lateral view of the embodiment of the invention drawn in FIG. 13I and a superior view of a cross section of an IVD. The first end of the flexible longitudinal fixation component was passed through AF tissue adjacent to the aperture using the method taught in FIGS. 13A-I.

Figure 13K:
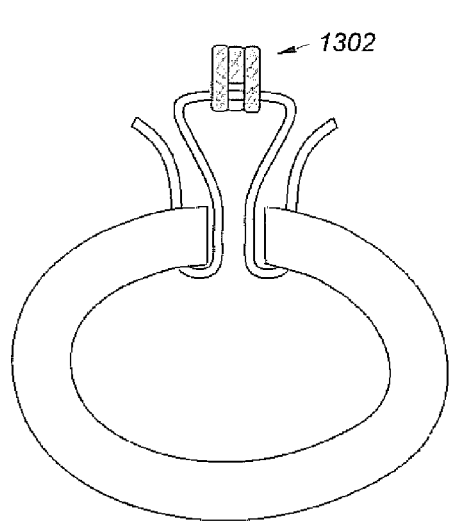
FIG. 13K is a lateral view of the embodiment of the invention drawn in FIG. 13J and a superior view of an axial cross section of the AF.

FIG. 13K is a lateral view of the embodiment of the invention drawn in FIG. 13J and a superior view of a cross section of an IVD. The second end of the flexible longitudinal fixation component was passed through AF tissue adjacent to the aperture using the method taught in FIGS. 13A-J.

Figure 13L:
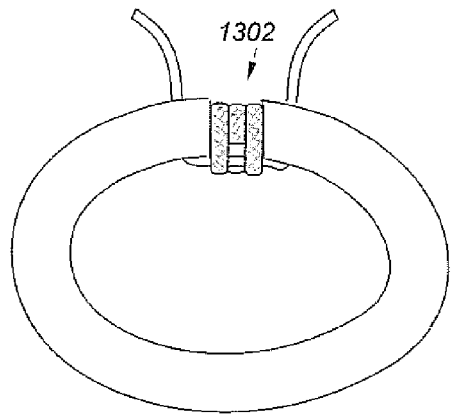
FIG. 13L is a lateral view of the embodiment of the invention drawn in FIG. 13K and a superior view of an axial cross section of the AF.

FIG. 13L is a lateral view of the embodiment of the invention drawn in FIG. 13K and a superior view of a cross section of an IVD. Tension on the ends of the flexible longitudinal component pulls the intra-aperture component 1302 into the aperture. Alternatively, the intra-aperture component could be inserted into the aperture then the ends of the flexible longitudinal fixation component could be pulled to tighten the flexible longitudinal component. The flexible longitudinal fixation component passes through the intra-aperture component closer to the inner edge (distal end) of the intra-aperture component than to the outer edge (proximal end) of the intra-aperture component. Such placement prevents rotation of the intra-aperture component about the longitudinal axis of the flexible longitudinal fixation component allowing the intra-aperture component to extend outside the AF, or more than 1 to 3 millimeters beyond the outer layer of the AF. Alternatively, as shown in FIG. 3A, the flexible longitudinal fixation component could pass through the center of the intra-aperture component. The ends of the flexible longitudinal component are preferably welded in the next step of the technique.

Figure 14A:
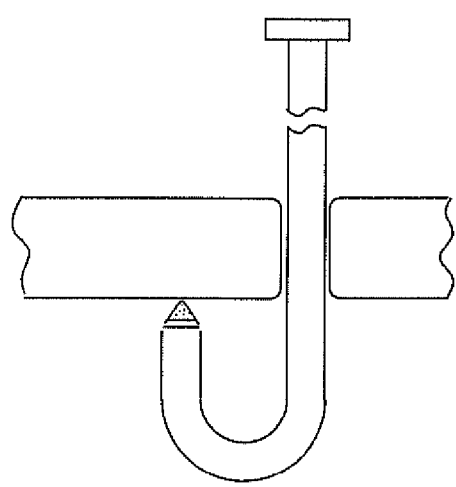
FIG. 14A is a lateral view of an alternative embodiment of the invention drawn in FIG. 13A and a cross section of a portion of the AF.
Figure 14B:
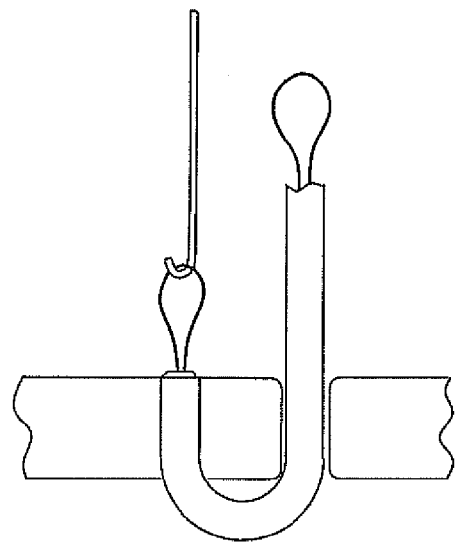
FIG. 14B is a lateral view of the embodiment of the invention drawn in FIG. 14A and a cross section of a portion of the AF.

FIG. 14A is lateral view of an alternative embodiment of the invention drawn in 13A and a superior view of a portion of the AF. The cannulated J-shaped component and a pointed flexible stylet were passed through an aperture and rotated about ninety degrees. FIG. 14B is lateral view of an alternative embodiment of the invention drawn in 14A and a superior view of a portion of the AF. A wire loop was push through the cannulated component after removing the stylet. The hook end of an instrument was passed into the first end of the wire loop.

Figure 14C:
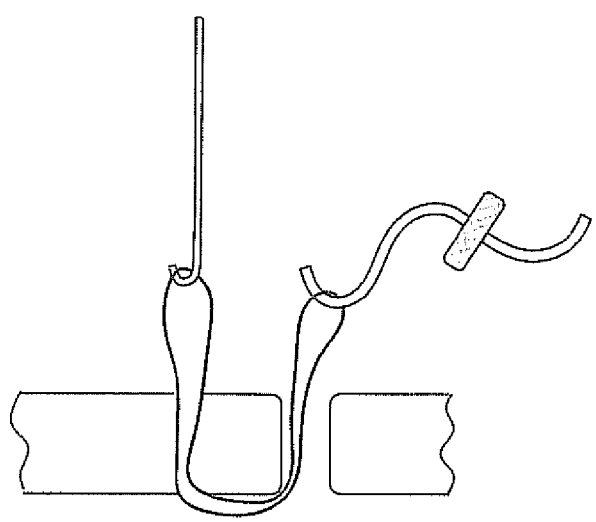
FIG. 14C is lateral view of the embodiment of the invention drawn in FIG. 14B and a cross section of a portion of the AF.

FIG. 14C is lateral view of an alternative embodiment of the invention drawn in FIG. 14B and a superior view of a portion of the AF. The wire loop was held by hook end of the instrument as the cannulated component was pulled from the IVD. The first end of a flexible longitudinal fixation component was passed through the wire loop. The first end of the flexible longitudinal fixation component is pulled through the AF as the wire loop is pulled from the IVD. The second end of the flexible longitudinal fixation component is passed through AF tissue on the opposite side of the aperture in the manner taught in FIGS. 14A-C.

Figure 15A:
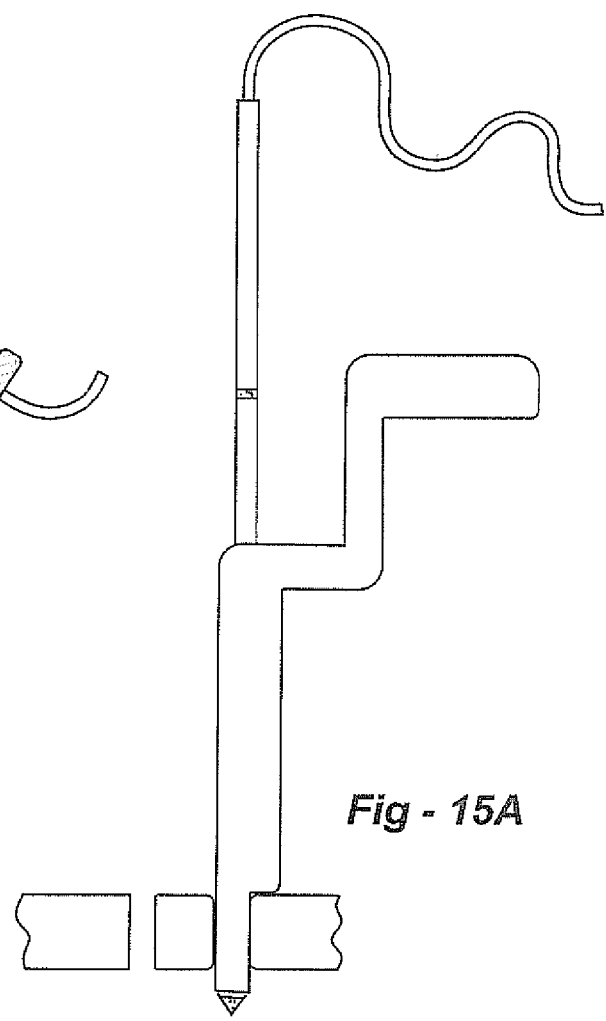
FIG. 15A is a lateral view of an alternative embodiment of the invention drawn in FIG. 12A and a superior view of a cross section of a portion of the AF.

FIG. 15A is a lateral view of an alternative embodiment of the invention drawn in 12A and a superior view of a cross section of a portion of the AF. A needle within a cannulated component and the distal end of the cannulated component were pushed through the AF on a first side of an aperture. A shoulder on the cannulated component limits the depth the tip of the instrument is inserted into the IVD. The shoulder is preferably 3 to 15 millimeters from the tip of the cannulated component. The shoulder is most preferably 5 to 10 millimeters from the tip of the cannulated component. The mark on the needle cooperates with the cannulated component to indicate the depth of needle insertion.

Figures 15B, 15C:
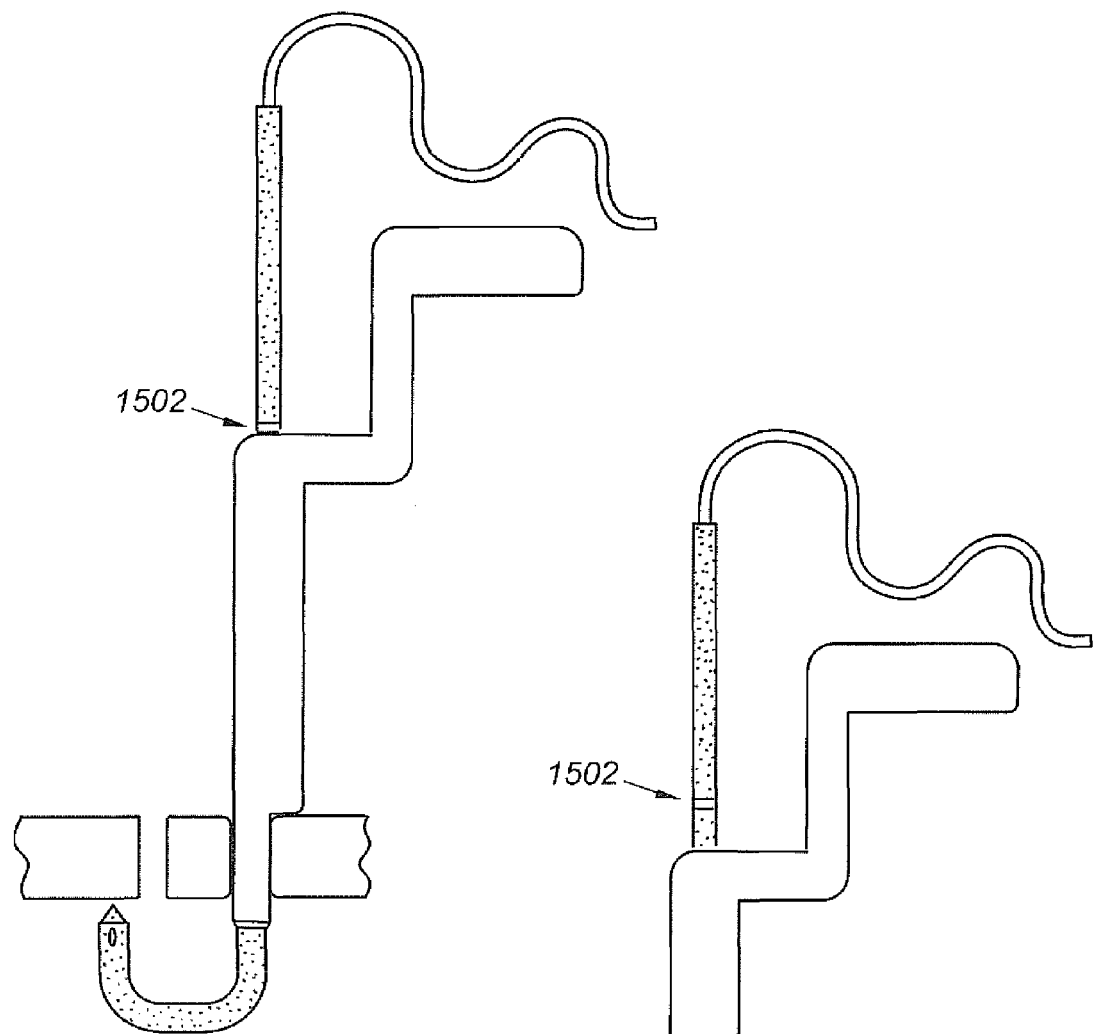
FIG. 15B is a lateral view of the embodiment of the invention drawn in FIG. 15A and a superior view of a cross section of a portion of the AF.
FIG. 15C is a lateral view of the embodiment of the invention drawn in FIG. 15B and a superior view of a cross section of a portion of the AF.

FIG. 15B is a lateral view of the embodiment of the invention drawn in FIG. 15A and a superior view of a cross section of a portion of the AF. The needle was advanced into the IVD. The needle is preferably made of shape memory material such as nitinal. The needle assumes a J-shape as it passes through the cannulated component and/or reacts to the heat of the IVD. An eyelet is seen near the tip of the needle. The vertical arm of the needle, with the eyelet, is preferably 5 to 25 millimeters long. The vertical arm of the needle, with the eyelet, is most preferably 10 to 20 millimeters long. The diameter of the needle is preferably 0.4 to 2.0 millimeters in diameter. Alternatively, the diameter of the needle could be 0.3, 2.1, 2.2, 2.3, 2.4, 2.5, or more millimeters in diameter. The needle is preferably between 6 and 30 centimeters long. Alternatively, the needle could be 4, 5, 31, 32, 33, 34, or more centimeters long. The proximal end of the needle could be more flexible than the distal end of the needle. Alternatively, other areas of the needle, such as the middle portion, could be the most flexible portion of the needle. The marking 1502 on the needle is seen adjacent to the cannulated component.

FIG. 15C is lateral view of the embodiment of the invention drawn in FIG. 15B and a superior view of a portion of the AF. The tip of the needle was pulled through the AF on the second side of the aperture.

Figures 15D, 15E, 15F, 15G:
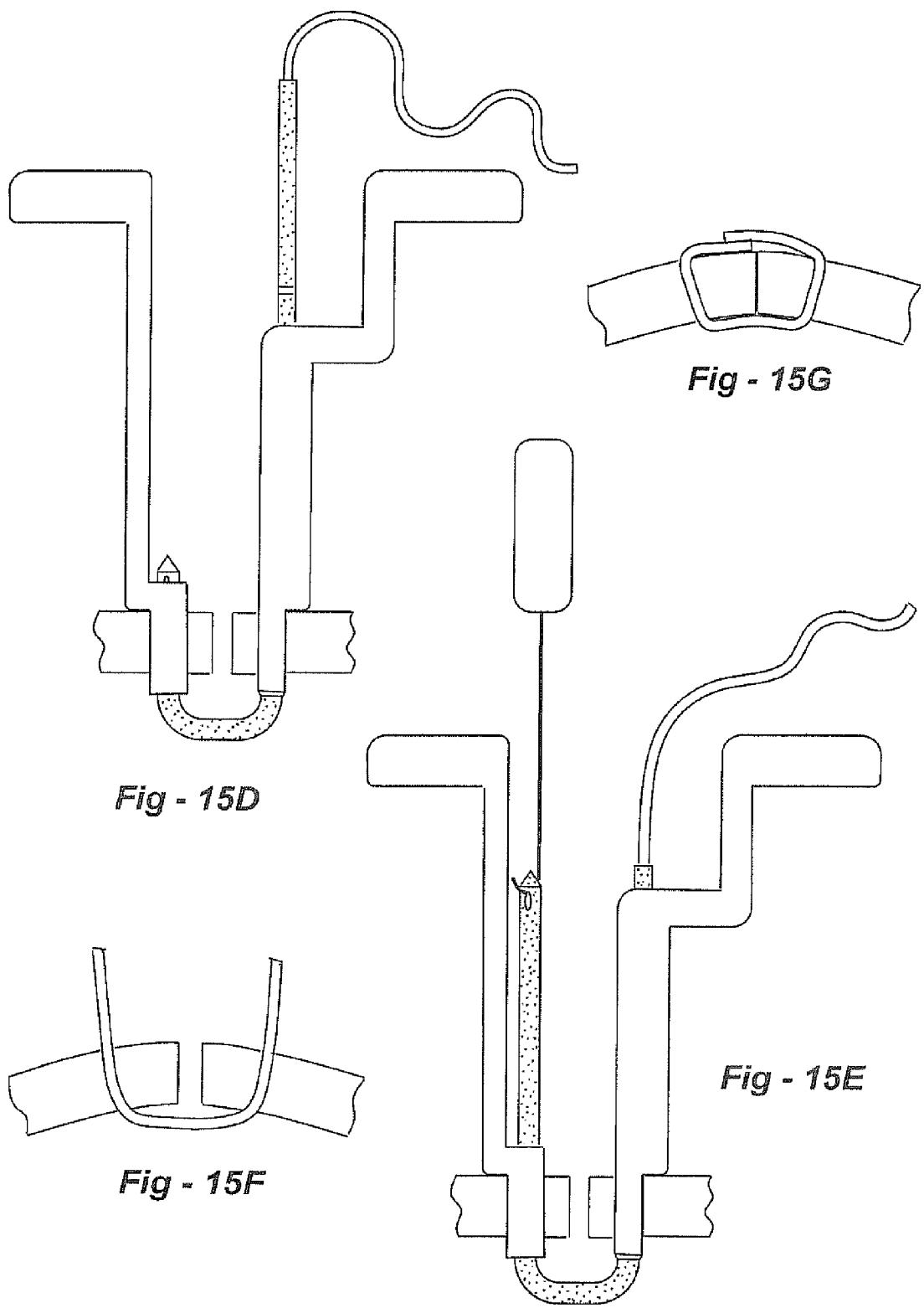
FIG. 15D is a lateral view of the embodiment of the invention drawn in FIG. 15C and a superior view of a cross section of a portion of the AF.
FIG. 15E is a lateral view of the embodiment of the invention drawn in FIG. 15D and a superior view of a cross section of a portion of the AF.
FIG. 15F is a lateral view of the embodiment of the invention drawn in FIG. 15E and a superior view of a cross section of a portion of the AF.
FIG. 15G is a lateral view of the embodiment of the invention drawn in FIG. 15F and a superior view of a cross section of a portion of the AF.

FIG. 15D is a lateral view of the embodiment of the invention drawn in FIG. 15C and a superior view of a portion of the AF. A second cannulated instrument was advanced over the tip of the needle. The cannulated portion of the second cannulated instrument is preferably 5 to 15 millimeters long. Alternatively, the cannulated portion of the second cannulated instrument may be 3, 5, 16, 17, 18, 19, 20, or more millimeters long. The second cannulated instrument has a shoulder that limits the depth the instrument is inserted into the IVD. The eyelet of the needle is seen above the cannulated portion of the second cannulated instrument.

FIG. 15E is a lateral view of the embodiment of the invention drawn in FIG. 15D and a superior view of a portion of the AF. A hook instrument is extending through the eyelet of the needle. The needle is advanced through the cannulated instruments by pulling on the tip of the needle or pushing on the shaft of the needle or both pushing and pulling on the needle. The cannulated instruments prevent injuring the AF as the needle is advanced through and between the cannulas.

FIG. 15F is a lateral view of the embodiment of the invention drawn in FIG. 15E and a superior view of a portion of the AF. The suture was cut to release the needle. The cannulated instruments were removed from the IVD.

FIG. 15G is a lateral view of the embodiment of the invention drawn in FIG. 15F and a superior view of a portion of the AF. The suture was welded under tension, which closes the aperture in the AF. The suture is preferably USP #2 weldable braided polyester. For example, the suture and thermal welding device supplied by Tornier (Edina, Minn.) could be used in this preferred embodiment of the invention. Alternative suture materials or alternative suture sizes could be used in alternative embodiments of the invention. For example, #2 nylon suture could be ultrasonically welded (Tornier, Edina, Minn.).

The invention claimed is:

1. A method of repairing or fortifying a void or defect in an anulus fibrosis, the method comprising:
    providing an intra-aperture component attached or coupled to one or more lengths of suture, the one or more lengths of suture having a resilient graspable portion;
    providing an instrument comprising:
        a shaft having a distal end, a proximal end and a longitudinal axis extending therethrough;
        a footplate having a distal end and a proximal end, the proximal end of the footplate being mounted to the distal end of the shaft, and the distal end of the footplate being laterally offset from the longitudinal axis of the shaft, the distal end of the footplate releasably carrying the one or more lengths of suture so that the graspable portion of the one or more lengths of suture projects laterally out of the distal end of the footplate and across the longitudinal axis of the shaft; and
        a needle having a distal end, a proximal end and a suture capture element disposed adjacent to its distal end, the needle being telescopically mounted to the shaft for movement along the longitudinal axis of the shaft;
    advancing the footplate through an aperture in the anulus fibrosis, with the graspable portion of the one or more lengths of suture being temporarily deflected by a rim portion of the anulus fibrosis adjacent to the aperture, whereby to permit the footplate and the graspable portion of the one more lengths of suture to enter the aperture, and with the graspable portion of the one or more lengths of suture thereafter returning to a position projecting across the longitudinal axis of the shaft;
    passing the needle through the rim of the anulus fibrosis adjacent to the aperture and grasping the graspable portion of the one or more lengths of suture; and
    pulling the graspable portion of the one or more lengths of suture through the anulus fibrosis from the inside out to secure the intra-aperture component on or within the void or defect.

2. The method of claim 1 wherein the graspable portion comprises a resilient ring attached to the one or more lengths of suture.

* * * * *